United States Patent
Nagashima et al.

(10) Patent No.: US 7,171,854 B2
(45) Date of Patent: Feb. 6, 2007

(54) NONDESTRUCTIVE INSPECTION APPARATUS AND NONDESTRUCTIVE INSPECTION METHOD USING ELASTIC GUIDED WAVE

(75) Inventors: Yoshiaki Nagashima, Hitachi (JP); Masahiro Koike, Hitachi (JP); Tetsuya Matsui, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/780,751

(22) Filed: Feb. 19, 2004

(65) Prior Publication Data

US 2004/0255678 A1    Dec. 23, 2004

(30) Foreign Application Priority Data

Jun. 20, 2003 (JP) .............................. 2003-175683

(51) Int. Cl.
*G01N 29/04* (2006.01)
(52) U.S. Cl. .......................................... 73/622; 73/612
(58) Field of Classification Search .................. 73/602, 73/620, 622, 627, 612
See application file for complete search history.

(56) References Cited

U.S. PATENT DOCUMENTS

| 5,269,485 | A |   | 12/1993 | Dwinell et al. |
| 5,513,532 | A | * | 5/1996 | Beffy et al. .................. 73/628 |
| 5,629,485 | A |   | 5/1997 | Rose et al. |
| 5,734,588 | A |   | 3/1998 | Rose et al. |
| 6,253,618 | B1 |  | 7/2001 | Wooh |
| 6,578,422 | B2 | * | 6/2003 | Lam et al. .................... 73/622 |
| 2002/0062693 | A1 |  | 5/2002 | Gorman et al. |
| 2002/0088281 | A1 |  | 7/2002 | Gorman |

FOREIGN PATENT DOCUMENTS

| JP | 10-185884 | 7/1998 |
| JP | 10-507530 | 7/1998 |
| JP | 11-223622 | 8/1999 |
| JP | 2002-236113 | 8/2002 |
| JP | 2003-57213 | 2/2003 |
| WO | WO 96/12951 | 5/1996 |
| WO | WO 02/008746 A3 | 1/2002 |

OTHER PUBLICATIONS

J.L. Rose, "Ultrasonic Waves in Solid Media." 1999, pp. 159-162.

* cited by examiner

*Primary Examiner*—John E. Chapman
(74) *Attorney, Agent, or Firm*—Dickstein Shapiro LLP

(57) ABSTRACT

A nondestructive inspection apparatus using a guided wave having waveform forming part that form a transmission waveform; a transmitting element for generating a guided wave within an object under inspection; a receiving element for receiving a reflection wave of the guided wave from an inspection region of the object under inspection; an analyzing element for outputting inspection information which is acquired based upon the reception waveform of the reflection wave received by the receiving element; and a display for displaying the inspection information.

18 Claims, 17 Drawing Sheets

FIG.4A

| INSPECTION CONDITION SETTING WINDOW |||
|---|---|---|
| PIPE WALL THICKNESS OF PIPE ARRANGEMENT | 6 mm ||
| MATERIAL | ∨ CARBON STEEL<br>STAINLESS STEEL<br>ALUMINUM ||
| SOUND VELOCITY OF LONGITUDINAL WAVE | 5940 m/s ||
| SOUND VELOCITY OF SHEAR WAVE | 3260 m/s ||
| INSPECTION REGION<br>(DISTANCE FROM ELEMENT) | 500 mm | ~ 1500 mm |

FIG.4B

| REFERENCE WAVEFORM SELECTING/DISPLAY WINDOW |||
|---|---|---|
| REFERENCE WAVEFORM | ∨ TONE BURST WAVE<br>GAUSSIAN ENVELOPE<br>RECTANGULAR WAVE | REFERENCE WAVEFORM PREVIEW |
| CYCLE NUMBER | 4 ||
| CENTER FREQUENCY | 500 kHz ||

FIG.5

| TRANSMISSION WAVEFORM DISPLAY WINDOW |||
|---|---|---|
| INSPECTION REGION | 500 mm ~ 1500 mm | INSPECTION SEGMENT INDICATOR<br>0 — 5000 |
| SEGMENT DIVISION | YES<br>∨ NO | SEGMENT CENTER 1000 mm<br>TRANSMISSION WAVEFORM PREVIEW |

REFERENCE WAVEFORM
u(t)

CALCULATED WAVEFORM WHEN
GUIDED WAVE OF REFERENCE
WAVEFORM "u(t)" TRANSMITTED AT
x=0 IS REACHED TO POSITION OF x=2d
u(2d,t)

$t_{max} = 2d/c_{min}$

TRANSMISSION WAVEFORM
$u'(t) = u(2d, t_{max}-t)$

CALCULATED WAVEFORM WHEN
GUIDED WAVE OF TRANSMISSION
WAVE "u'(t)" TRANSMITTED AT
x=0 IS REACHED TO POSITION OF x=2d

TRANSMISSION WAVEFORM AUTOMATICALLY FORMED UNDER INSPECTION REGION FROM 500 mm TO 150 mm

INSPECTION RESULT USING NORMAL TRANSMISSION WAVEFORM

INSPECTION RESULT USING AUTOMATICALLY FORMED TRANSMISSION WAVEFORM

FIG.13A

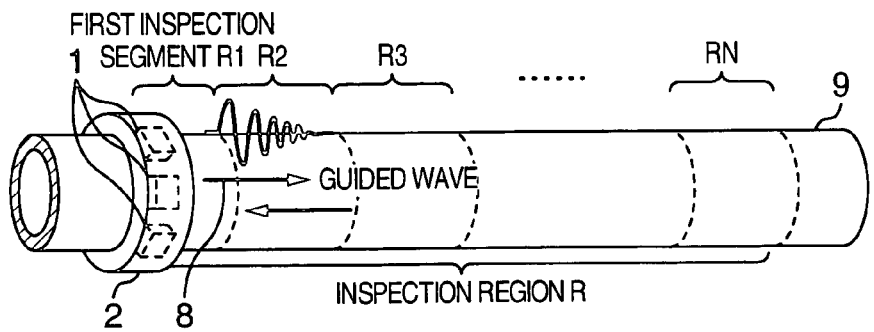

FIG.13B

RECEPTION WAVEFORM RECEIVED
WHEN TRANSMISSION WAVEFORM
HAVING HIGH SENSITIVITY WITH
RESPECT TO SECOND INSPECTION
SEGMENT (R2) IS APPLIED
TO GUIDED WAVE TRANSMITTING/
RECEIVING ELEMENT 1

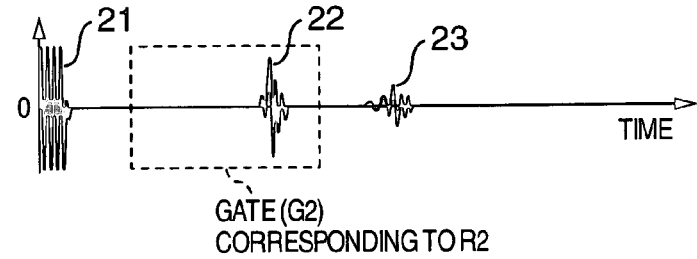

FIG.13C

RECEPTION WAVEFORM RECEIVED
WHEN TRANSMISSION WAVEFORM
HAVING HIGH SENSITIVITY WITH
RESPECT TO THIRD INSPECTION
SEGMENT (R3) IS APPLIED
TO GUIDED WAVE TRANSMITTING/
RECEIVING ELEMENT 1

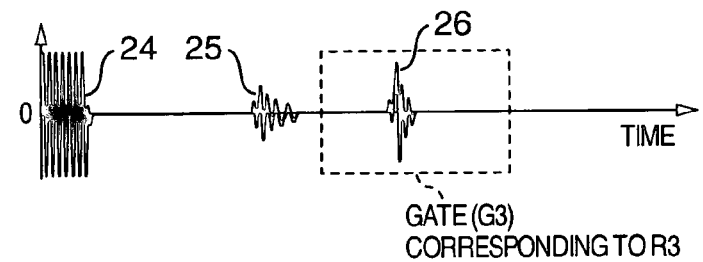

FIG.13D

COUPLED WAVEFORM

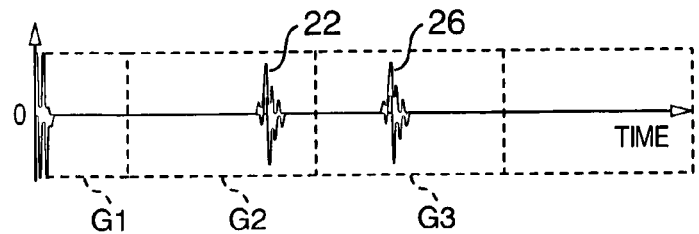

TRANSMISSION WAVEFORM IN WHICH REFLECTION WAVE
FROM POSITION OF DISTANCE 500 mm BECOMES HIGH AMPLITUDE

TRANSMISSION WAVEFORM IN WHICH REFLECTION WAVE
FROM POSITION OF DISTANCE 1000 mm BECOMES HIGH AMPLITUDE

TRANSMISSION WAVEFORM IN WHICH REFLECTION WAVE
FROM POSITION OF DISTANCE 2000 mm BECOMES HIGH AMPLITUDE

FIG.15A
REFLECTION WAVEFORM REFLECTED FROM DEFECT LOCATED AT POSITION BY DISTANCE 500 mm IN CASE THAT TRANSMISSION WAVEFORM IS TRANSMITTED IN WHICH REFLECTION WAVE REFLECTED FROM POSITION BY DISTANCE 500 mm BECOMES HIGH AMPLITUDE

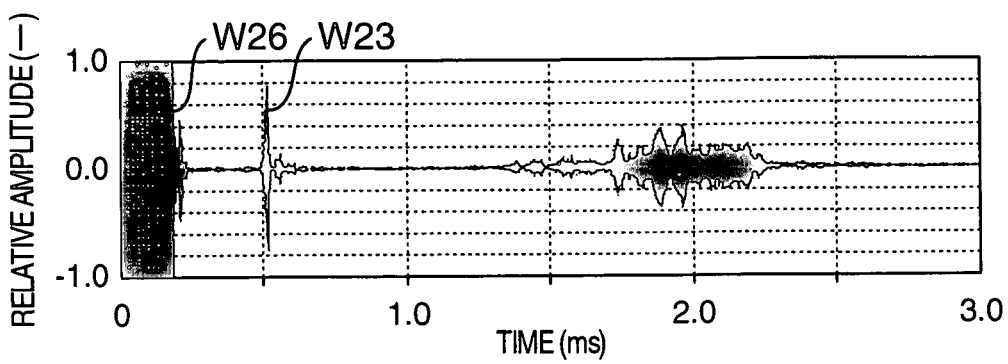

FIG.15B
REFLECTION WAVEFORM REFLECTED FROM DEFECT LOCATED AT POSITION BY DISTANCE 1000 mm IN CASE THAT TRANSMISSION WAVEFORM IS TRANSMITTED IN WHICH REFLECTION WAVE REFLECTED FROM POSITION BY DISTANCE 1000 mm BECOMES HIGH AMPLITUDE

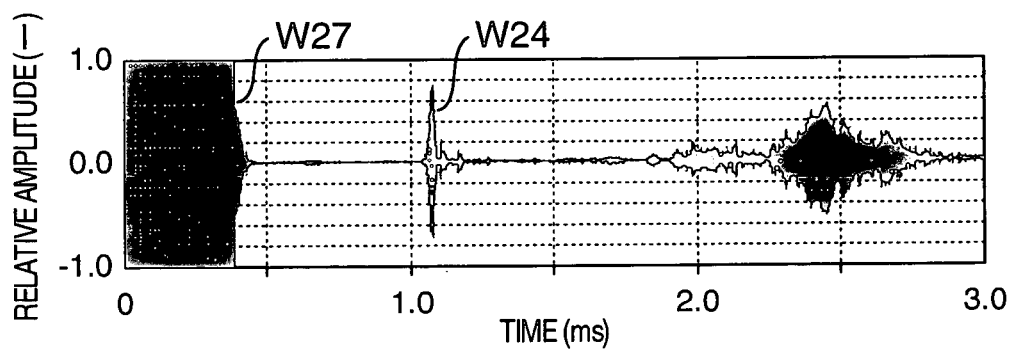

FIG.15C
REFLECTION WAVEFORM REFLECTED FROM DEFECT LOCATED AT POSITION BY DISTANCE 2000 mm IN CASE THAT TRANSMISSION WAVEFORM IS TRANSMITTED IN WHICH REFLECTION WAVE REFLECTED FROM POSITION BY DISTANCE 2000 mm BECOMES HIGH AMPLITUDE

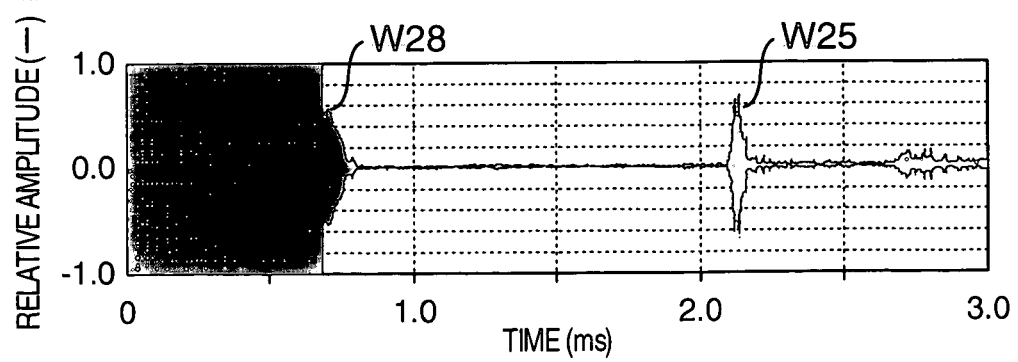

DISPERSION AMPLITUDE
CORRECTION CURVE

COUPLED WAVEFORM

COUPLED WAVEFORM AFTER
DISPERSION AMPLITUDE
CORRECTION

COUPLED WAVEFORM
OF CHANNEL 1

INSPECTION IMAGE OBTAINED
BY SYNTHESIZING
COUPLED WAVEFORMS
OF ALL CHANNELS

TONE BURST WAVE (EXAMPLE OF 4 CYCLES)

NONDESTRUCTIVE INSPECTION APPARATUS AND NONDESTRUCTIVE INSPECTION METHOD USING ELASTIC GUIDED WAVE

BACKGROUND OF THE INVENTION

1. Field of the Invention

The present invention is related to a nondestructive inspection method and a nondestructive inspection apparatus, capable of inspecting deteriorations of pipe arrangements (pipe laying) in a batch manner over a long distance section, while using an elastic guided wave.

2. Description of the Related Art

As to pipe arrangements used in various sorts of construction plants, both inner surfaces and outer surfaces of these pipe arrangements are deteriorated, namely corrosion and erosion become conspicuous when a long time period has passed after constructions of these pipe arrangements. While these deteriorations are progressed, when the corrosion and the erosion may penetrate through pipe wall thicknesses of the pipe arrangements, there is a risk that leakage failures happen to occur. To avoid such a risk, the below-mentioned countermeasures are required. That is, conditions of pipe wall thicknesses of these pipe arrangements are evaluated by employing nondestructive means, and thus, these deteriorated pipe arrangements are repaired and/or replaced by new pipe arrangements before leakage failures happen to occur.

As a typical nondestructive measuring means using sound waves, an ultrasonic thickness gauge is known. Generally speaking, such an ultrasonic thickness gauge corresponds to an apparatus in which while employing an ultrasonic sensor constituted by piezoelectric elements capable of mutually converting electric energy and acoustic energy so as to energize bulk waves (namely, elastic waves known as longitudinal waves and shear waves) within a pipe arrangement under inspection, elastic waves reflected from a bottom plane of the pipe arrangement is received by either the same ultrasonic sensor, or another ultrasonic sensor in order to measure pipe wall thicknesses of this pipe arrangement.

This ultrasonic measuring apparatus is capable of measuring the pipe wall thickness of the pipe arrangement in high precision due to such a measuring basic idea, namely, a reception time of received wave is converted into a pipe wall thickness. On the other hand, an inspection range of this ultrasonic measuring apparatus is limited only to such a range substantially equal to a dimension of the ultrasonic sensor. When an inspection-required range is widened as known as a long-distance pipe arrangement, this ultrasonic measuring apparatus owns the following drawback. That is, since a total number of measuring points is increased, very long inspection time is necessarily required for the wide inspection-required range. Further, lengthy time is required so as to preparate/install/uninstall the ultrasonic measuring apparatus with respect to such a pipe arrangement having a problem of accessible characteristics, for example, a pipe arrangement equipped with a heat insulating material, a buried pipe arrangement, and a vertical pipe arrangement.

As one of the countermeasures capable of solving such a problem, there is such an inspection method that while a guided wave is employed, a long distance section of pipe arrangement is inspected in a batch manner. This guided wave implies such an elastic wave which is formed by interference occurred between a longitudinal wave and a shear wave, which are propagated with performing reflections and mode conversions through an object having a boundary plane such as a pipe arrangement and a plate. This inspection method corresponds to such an inspection method for utilizing a feature. That is, the guided waves are reflected at a position of the pipe arrangement, in which a sectional area of this pipe arrangement along the circumferential direction is varied. In this inspection method, while a single mode of guided waves which are symmetrical with respect to a center axis of the pipe arrangement is propagated along the axial direction of the pipe arrangement, either a reduced pipe wall thickness or a dimension of a defect, and an axial position are measured based upon an amplitude of this reflection wave and an appearing time of this reflection wave. A reflection wave may be acquired from a welding line except for either the reduced pipe thickness or the defect. These reflection waves reflected from the welding line and the reduced pipe wall thickness, or the defect may be discriminated from each other based upon a feature (more specifically, see patent publication 1, JP-A-10-507530). That is, as this feature, the reflection wave reflected from either the reduced pipe wall thickness or the defect is vibrated in a non-axisymmetric manner with respect to the center axis of the pipe arrangement, whereas the reflection wave reflected from the welding line is vibrated in an axisymmetric manner with respect to this center axis.

Also, another inspection apparatus for inspecting a pipe arrangement using an elastic wave is known (in particular, see patent publication 2, JP-A2002-236113). In this inspection apparatus, while a correlative relationship between a detection signal and a reference signal is acquired, the elastic wave is capable of specifying a position of a defect in high precision based upon a maximum turning value of this correlative relationship.

The above-described conventional technique has described that the tone burst wave (tone burst wave in 4 cycles is exemplified in FIG. 26) is applied to the excitation ring of the guided wave. However, the guided wave represents such a characteristic that the sound velocity is varied in response to the frequency (will be referred to as "dispersion" hereinafter, and this characteristic will be referred to as "dispersion characteristic" hereinafter). This dispersion implies such an operation that the sound velocity is varied in response to the frequency. As a consequence, when such a guided wave available in the frequency range where the group velocity is not constant is utilized, the detection performance capable of detecting the pipe wall thickness and the defect, which are located far from the sensor, is lowered. The group velocity implies a velocity at which a wave packet is propagated.

This phenomenon will now be explained in detail. For example, in the case that a material of a pipe arrangement is made of a carbon steel (sound velocity of longitudinal wave=5940 m/s, and sound velocity of shear wave=3260 m/s); an outer diameter of this pipe arrangement is 114.3 mm; and a wall thickness thereof (ratio of wall thickness to outer diameter is 0.052) is 6 mm, a relationship between a product of the frequency and the wall thickness, and a sound velocity of a guided wave may be obtained as illustrated in FIG. 27 from the theoretical basis. FIG. 27A indicates a phase velocity in which reference numeral "$51a$" is called as an $L(0, 1)$ mode; reference numeral "$52a$" is referred to as an $L(0, 2)$ mode; reference numeral "$53a$" is called as an $L(0, 3)$ mode; and reference numeral "$54a$" is referred to as an $L(0, 4)$ mode. Then, the larger the numeral "m" indicated by $L(n, m)$ becomes, the more the displacement distribution along the plate thickness direction becomes complex. FIG. 28 schematically shows a feature of displacement, depending upon the modes. FIG. 28 indicates the L(0, 1) mode, the L(0, 2) mode, and the L(0, 3) mode in this order from the upper mode.

FIG. 27B shows a group velocity in which reference numeral "51b" shows the L(0, 1) mode; reference numeral "52b" indicates the L(0, 2) mode; reference numeral "53b" shows the L(0, 3) mode; and reference numeral "54b" indicates the L(0, 4) mode. In the case of the L(0, 2) mode, the group velocity 52b becomes substantially constant in such a frequency range lower than, or equal to approximately 150 KHz (namely, frequency×wall thickness=0.9 MHzmm), but the group speed "52b" is largely changed in response to the frequencies between 300 KHz and 500 KHz (namely, frequency×wall thickness=1.8 to 3.0 MHzmm).

In order to verify this theoretical basis, the following experiment was carried out. That is, as to a pipe arrangement having an outer diameter of 114.3 mm, a wall thickness of 6 mm, and a length of 5500 mm, a defect was made at a position separated from an edge portion thereof by 1500 mm; the L(0, 2) mode guided wave having a center frequency of 500 KHz was transmitted; and then, reflection waveforms reflected from this defect was detected. This wave detection result is shown in FIG. 29. FIG. 29A explanatorily shows a reflection waveform in such a case that the sensor is installed at a position separated from the defect by 200 mm (namely, at position separated from edge portion of pipe arrangement by 1700 mm); reference numeral "61" indicates a reflection wave reflected from the defect; and reference numeral "62" shows a reflection wave reflected from the edge portion of the pipe arrangement. FIG. 29B explanatorily shows a reflection waveform in such a case that the sensor is installed at a position separated from the defect by 1000 mm (namely, at position separated from edge portion of pipe arrangement by 2500 mm); reference numeral "63" indicates a reflection wave reflected from the defect; and reference numeral "64" shows a reflection wave reflected from the edge portion of the pipe arrangement. When the reflection waveform "61" reflected from the defect is compared with the reflection waveform "63" reflected from the defect, the duration time of the wave motion as to the reflection wave "63" (namely, distance between sensor and defect is longer) apparently becomes longer. This is because the sound velocity represents different dispersion characteristics, depending upon the frequencies, as previously explained. When such a frequency range is used, the energy of the guided wave is broadened on the time axis, and the amplitude of this guided wave is lowered in accordance with the length of the propagation distance. In particular, a certain detecting problem may be conducted as to detections of a very small crack and of a reduced wall thickness of the pipe arrangement.

Generally speaking, a frequency range in which a sound velocity is dispersed may appear in a high frequency range. As a result, one of countermeasures is to lower the frequencies. However, in this countermeasure, since a wavelength becomes long at the same time, sensitivities with respect to the very small defects are deteriorated.

SUMMARY OF THE INVENTION

An object of the present invention is to provide a nondestructive inspection method and a nondestructive inspection apparatus, capable of compensating for lowering of an amplitude caused by dispersion and capable of inspecting an object under inspection over a long distance section thereof in a batch manner, although a relatively higher frequency range where a sound velocity is dispersed by a frequency is utilized.

To achieve the above-described object of the present invention, a nondestructive inspection apparatus, according to an aspect of the present invention, is featured by such a nondestructive apparatus using a guided wave, comprising: waveform forming means for forming a transmission waveform by employing a reference waveform; a transmitting element for generating a guided wave within an object under inspection based upon the transmission waveform; a receiving element for receiving a reflection wave of the guided wave from an inspection region of the object under inspection; analyzing means for outputting inspection information which is acquired based upon the reception waveform of the reflection wave received by the receiving element; and display means for displaying thereon the inspection information.

Similarly, a nondestructive inspection method, according to another aspect of the present invention, is featured by such a nondestructive inspection method comprising: a step for forming a transmission waveform by employing a reference waveform; a step for generating a guided wave within an object under inspection based upon the transmission waveform; a step for receiving a reflection wave of the guided wave from an inspection region of the object under inspection by a receiving element; a step for acquiring inspection information which is acquired based upon the reception waveform of the reflection wave received by the receiving element; and a step for displaying thereon the inspection information.

Other objects, features and advantages of the invention will become apparent from the following description of the embodiments of the invention taken in conjunction with the accompanying drawings.

BRIEF DESCRIPTION OF THE DRAWINGS

FIG. 4A and FIG. 4B illustratively show a display example as to both an inspection condition setting window and a reference waveform selecting/display window used in the first embodiment of the present invention.

FIG. 5 illustratively shows a display example of a transmission waveform display window in the first embodiment of the present invention.

FIG. 13A to FIG. 13D are explanatory diagrams for explaining steps capable of acquiring an inspection result by coupling received waveforms to each other.

FIG. 15A to FIG. 15C are diagrams for showing results of tests capable of improving sensitivities with respect to defects located in a specific inspection segment in the case that a guided wave is energized in such a manner that a duration time of a signal is reduced when reflection waveforms reflected from the specific inspection segment are received.

DESCRIPTION OF THE EMBODIMENTS

Figure 1:
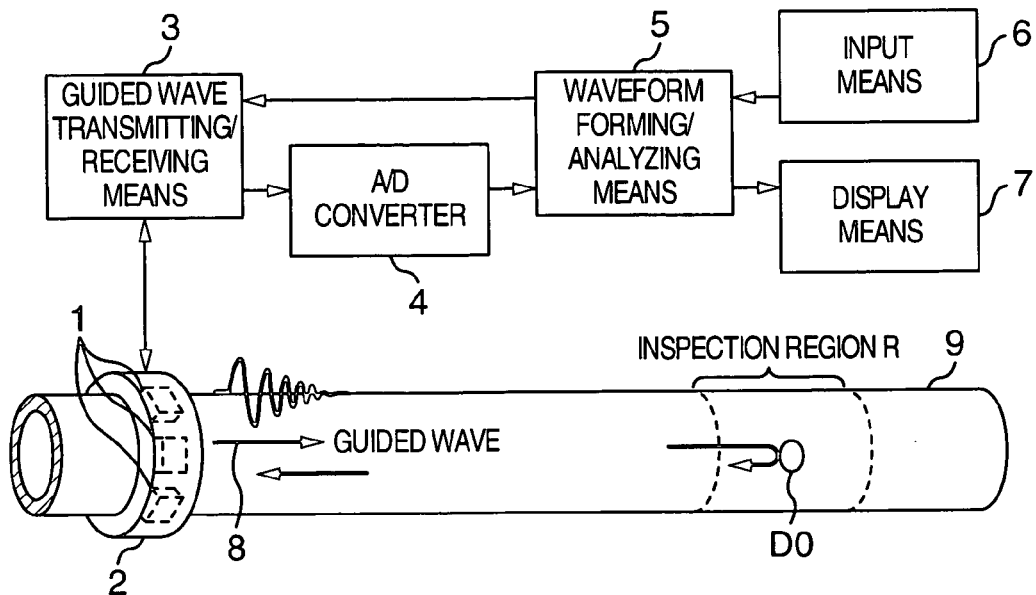
FIG. 1 is a schematic block diagram for showing a pipe arrangement inspecting apparatus according to a first embodiment of the present invention.
Figure 2:
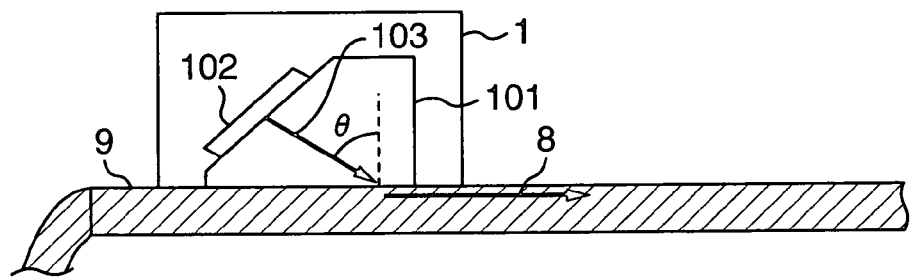
FIG. 2 is an explanatory diagram for explaining a structural example of a guided wave transmitting/receiving element employed in the pipe arrangement inspecting apparatus of FIG. 1.
Figure 3:
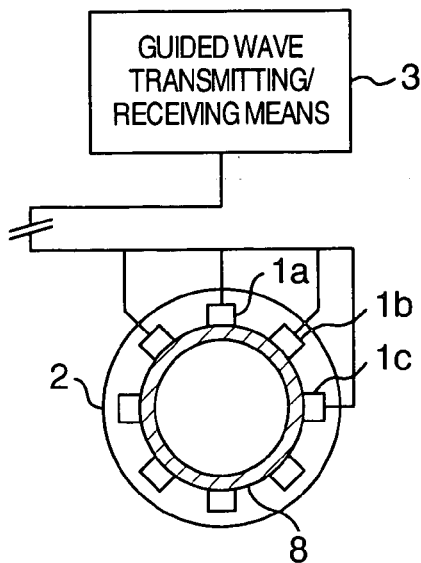
FIG. 3 is a connection diagram for connecting a guided wave transmitting/receiving means to a guided wave transmitting/receiving element in the pipe arrangement inspecting apparatus of the first embodiment.

Referring now to FIG. 1 to FIG. 3, an arrangement of a pipe arrangement (pipe laying) inspecting apparatus corresponding to a nondestructive inspection apparatus, according to a first embodiment of the present invention. FIG. 1 is a schematic block diagram of the pipe arrangement inspecting apparatus according to this first embodiment. In this drawing, reference numeral 1 shows a guided wave transmitting/receiving element, namely, such an element which is commonly used as a transmitting element and a receiving element. The transmitting element is employed when a guided wave is generated, whereas the receiving element is employed when a reflection wave of this guided wave is received. Also, reference numeral 2 indicates a transmitting/receiving element ring, reference numeral 3 shows guided wave transmitting/receiving means, and reference numeral 4 represents an AdD converter. Reference numeral 5 shows waveform forming/analyzing means, reference numeral 6 indicates input means, and reference numeral 7 represents display means. It should be understood that a guided wave is defined as an elastic wave, namely an ultrasonic wave. This elastic wave is formed by interference occurred between longitudinal waves and shear waves, which are propagated through an object having a boundary plane such as an arranged pipe and a plate, while modes of the longitudinal waves and the shear waves are converted, and also both the longitudinal waves and the shear waves are reflected. In the guided wave transmitting/receiving element 1, a commonly-used piezoelectric element is employed as the transmitting element when the guided wave is transmitted, and also, is employed as the receiving element when the reflection wave is received. Alternatively, while a piezoelectric element exclusively used as a transmitting element is provided in the vicinity of a piezoelectric element exclusively used as a receiving element, these transmitting element and receiving element may be exclusively used, depending upon a transmission mode and a reception mode.

The guided wave transmitting/receiving element 1 corresponds to such an element capable of generating guided waves in a pipe arrangement (pipe laying) 9, and is constituted by, for example, a piezoelectric element. The guided wave transmitting/receiving element 1 is arranged in contact with the pipe arrangement 9, and is electrically connected via a coaxial cable to the guided wave transmitting/receiving means 3. The transmitting/receiving element ring 2 corresponds to such a jig which grips a plurality of guided wave transmitting/receiving elements 1 on a peripheral portion of the pipe arrangement 9 in a circular ring shape. Preferably, this transmitting/receiving ring 2 has such a structure that the plural guided wave transmitting/receiving elements 1 are stored in an equi-interval along a circumferential direction, and is detachably mounted with respect to the pipe arrangement 9. The transmitting/receiving element ring 2 has such a ½-divided construction that a ring-shaped frame is cut along a diameter of this ring. The ½-divided edges are coupled to each other by way of a screw so as to be assembled in a ring shape. As a result, when the ring-shape frame is assembled along the outer peripheral portion of the pipe arrangement 9, this transmitting/receiving element ring 2 is mounted on the outer peripheral portion of the pipe arrangement 9. A plurality of guided wave transmitting/receiving elements 1 are stored in an inner side of the ring-shaped frame of this transmitting/receiving element ring 2, and are supported by such a spring which is extended/compressed from the ring-shaped frame of the transmitting/receiving element ring 2 toward the outer peripheral plane of the pipe arrangement 9. As a consequence, when this transmitting/receiving element ring 9 is mounted on the outer peripheral plane of the pipe arrangement 9, a plurality of guided wave transmitting/receiving elements 1 are depressed against the outer peripheral plane of the pipe arrangement 9 by way of this spring, so that guided waves may be readily generated from these guided wave transmitting/receiving elements 1 with respect to the pipe arrangement 9.

The guided wave transmitting/receiving means 3 corresponds to such a means for applying a transmission waveform to the guided wave transmitting/receiving element 1 so as to transmit guided waves, and furthermore, for amplifying a reception waveform received from the guided wave transmitting/receiving element 1. This guided wave transmitting/receiving means 3 is connected to the waveform forming/analyzing means 5 in such a manner that digital data can be communicated, and also, is connected via a coaxial cable so as to supply the reception waveform to the A/D converter 4. This guided wave transmitting/receiving means 3 may be constituted by, for instance, either a synthesizer capable of arbitrarily setting a frequency of a transmission waveform or an arbitrary waveform generator, a power amplifier which amplifies these signals of the synthesizer and the arbitrary waveform generator, and either a commercially-available ultrasonic receiver or a broadband amplifier.

The A/D converter 4 owns a function capable of converting an analog signal into a digital signal, and is connected in such a manner that a received waveform (analog waveform) of a guided wave outputted from the guided wave transmitting/receiving means 3 is communicated as a digital waveform to the waveform forming/analyzing means 5. As this A/D converter 4, for example, on-board type A/D converters which are assembled in a computer and/or a commercially-available oscilloscope may be used.

The waveform forming/analyzing means 5 corresponds to such a means that a transmission waveform is formed, a received waveform is analyzed, and an entire operation of the pipe arrangement inspecting apparatus of this embodiment is controlled. The waveform forming/analyzing means 5 is arranged by a computer, or the like, and is connected to input means 6 and display means 7 such as a CRT. The input means 6 is a keyboard, or the like, which accepts an instruction of an operator.

Next, a structural example of the above-explained guided wave transmitting/receiving element 1 will now be explained with reference to FIG. 2. In this drawing, reference numeral 101 shows acrylic resin, reference numeral 102 represents a thickness vibrating element (piezoelectric element), and reference numeral 103 indicates a longitudinal wave transmitted from the thickness vibrating element 102. Also, reference numeral 9 shows a pipe arrangement, and reference numeral 8 is a guided wave which is propagated through the pipe arrangement 9. The thickness vibrating element 102 is arranged at an inclined angle in such a manner that the longitudinal wave 103 is entered with respect to the pipe arrangement 9 at an incident angle "$\theta$", which is calculated in accordance with the Snall's law $\theta = \sin^{-1}(Cw/c(\omega))$ under such a condition that a refraction angle is set to 90 degrees. In this Snall's law, symbol "Cw" indicates a longitudinal-wave sound velocity of the acrylic resin, and symbol "$c(\omega)$" shows a phase velocity of a mode which is wanted to be generated, and symbol "$\omega$" indicates a central angular frequency of a guided wave.

Figure 27A:
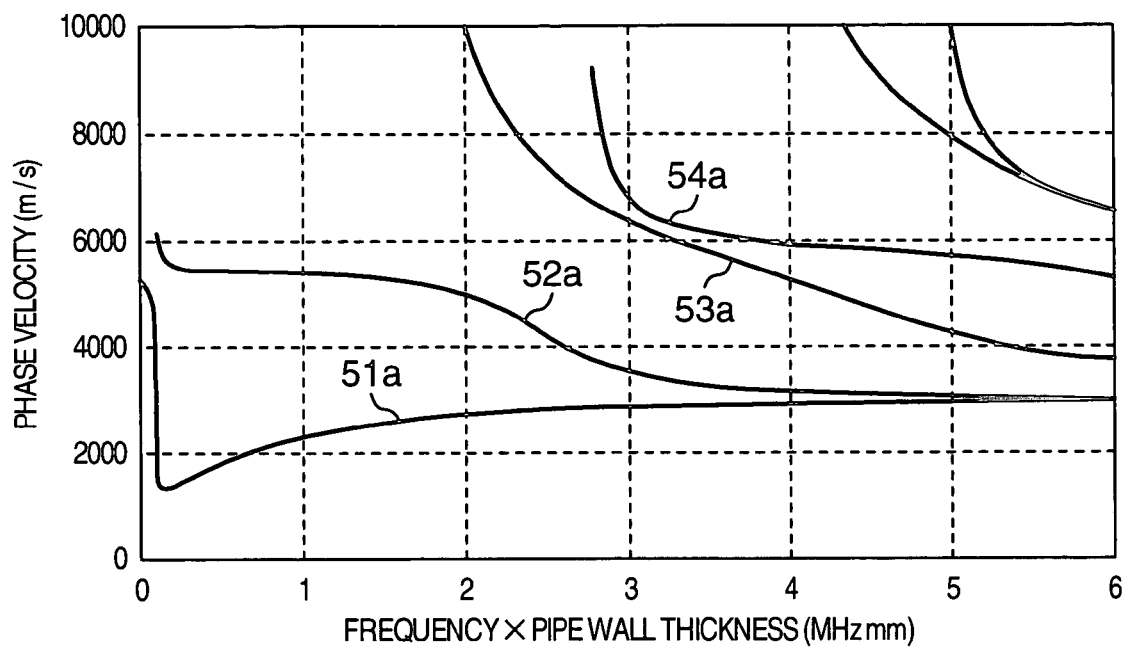
FIG. 27A and FIG. 27B are explanatory diagrams for explaining that velocities (group velocities) of guided waves in a plurality of vibration modes own dispersion characteristics which may change, depending upon a frequency, and also, a group velocity in each of the vibration modes may be exclusively determined by a product between a pipe wall thickness and a frequency.

Assuming now that the longitudinal-wave sound velocity of the acrylic resin is equal to, for example, 2720 m/s, since the phase velocity is equal to 3480 m/s (see FIG. 27A) under frequency of L(0, 2) mode×pipe wall thickness=3 MHzmm, the incident angle "$\theta$" may be determined as 51 degrees. It should be noted that the material of the structural element 101 is not limited only to acrylic resin, but also other resin-series materials such as polystyrene may be used.

FIG. 3 is a connection diagram as to both the guided wave transmitting/receiving means 3 and the guided wave transmitting/receiving element 1. In this drawing, reference numerals 1$a$, 1$b$, 1$c$ indicate guided wave transmitting/receiving elements. All of these guided wave transmitting/receiving elements 1$a$, 1$b$, 1$c$ are connected parallel to the guided wave transmitting/receiving means 3. As a result, a transmission waveform applied from the guided wave transmitting/receiving means 3 can vibrate all of these guided wave transmitting/receiving elements 1$a$, 1$b$, 1$c$ at the same time.

Figure 6:
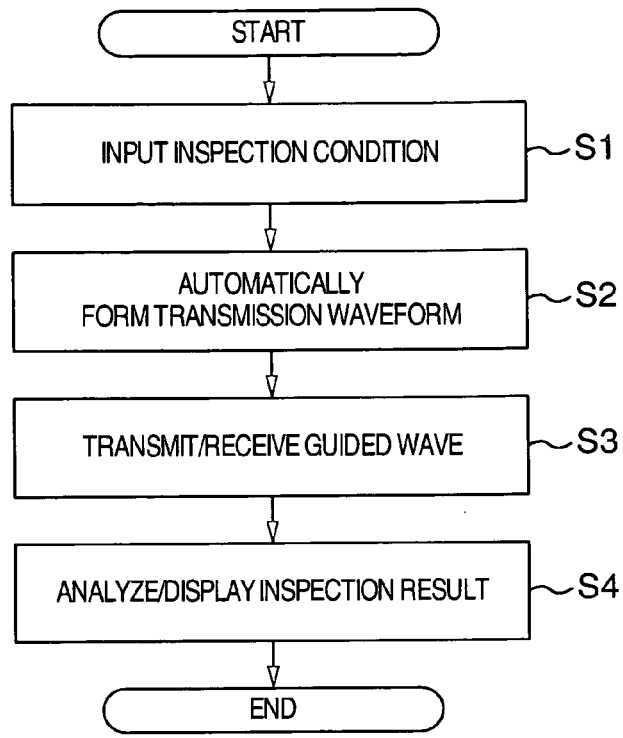
FIG. 6 is a flow chart for describing an internal process operation executed in a waveform forming/analyzing means when a pipe arrangement is inspected by the pipe arrangement inspecting apparatus according to the first embodiment of the present invention.

Next, operations of the pipe arrangement inspecting apparatus according to the first embodiment of the present invention will now be described with reference to FIG. 1, FIG. 4, FIG. 5, FIG. 7, and a flow chart of FIG. 6. This flow chart of FIG. 6 indicates an internal process operation of the waveform forming/analyzing means 5. In a first step S1, the waveform forming/analyzing means 5 requests a user to input an inspection condition. At this time, while an inspection condition setting window shown in FIG. 4A is displayed on the display means, the waveform forming/analyzing means 5 requests the user to input a pipe wall thickness, a material, or a sound velocity (sound velocities of longitudinal wave and shear wave) of a pipe arrangement, and an inspection region (namely, distance measured from guided wave transmitting/receiving element 1 is defined as origin, i.e., zero mm). Although not described in FIG. 4, the waveform forming/analyzing means 5 may alternatively request the user to input an outer diameter of the pipe system.

In the case that the material of the pipe system is entered, the waveform forming/analyzing means 5 calculates both a sound velocity of a longitudinal wave and a sound velocity of a shear wave as to the entered material by referring to a database in which previously-stored materials correspond to sound velocities. Also, if necessary, while a reference waveform selecting/display window shown in FIG. 4B is displayed, a plurality of subjects of reference waveforms are displayed, which constitute references of transmission waveforms (will be discussed later), and then, a selection of such a reference waveform subject is requested. Also, the waveform forming/analyzing means 5 requests the user to input a cycle number, and a center frequency, and displays a reference waveform as to the entered condition on a reference waveform preview so as to assist an input operation.

Also, while a transmission waveform display window shown in FIG. 5 is displayed on the display means 7, a user is required to select as to whether or not the inspection region is subdivided into a plurality of segments. In this first embodiment, the following explanations as to such a case that the inspection region is not subdivided into the plural segments (mark is checked on "NO") are made.

When all of these conditions are inputted, the waveform forming/analyzing means 5 automatically forms a transmission waveform (step S2). The automatic forming operation of the transmission waveform may be realized by that the below-mentioned formulae is installed in the software form in the waveform forming/analyzing means 5. Contents of the formulae will now be explained with reference to FIG. 7.

Figure 7A:
FIG. 7A to FIG. 7D are explanatory diagrams for explaining stages for calculating transmission waveforms.
Figure 7B:
Figure 7C:
Figure 7D:

At a first stage, the Fourier transform is performed based upon a formula (1) with respect to a reference waveform "u(t)" (see FIG. 7A) so as to calculate a complex Fourier component "U(ω)" A waveform shown in FIG. 7D corresponds to such a waveform which is intended to be received by a receiving element, and this waveform of FIG. 7D becomes a waveform equivalent to the reference waveform "u(t)."

$$U(\omega) = \frac{1}{2\pi} \int_{-\infty}^{\infty} u(t)e^{-i\omega t} dt \qquad \text{formula (1)}$$

Next, a phase delay is applied to the complex Fourier component "U(ω)", and an inverse Fourier transform is carried out with respect to the resulting complex Fourier component so as to calculate a calculated waveform "u(2d, t)" (see FIG. 7D) after the reference waveform "u(t)" is propagated over a distance "2d" (formula (2)). This phase delay corresponds to a time duration when the reference waveform "u(t)" is propagated in a reciprocating manner over a distance "d" (namely, distance defined from guided wave transmitting/receiving element 1 to center of inspection region "R"), namely a time duration when the reference waveform "u(t)" is propagated over the distance "2d." Finally, the calculated waveform "u(2d, t)" is time-inverted in accordance with the following formula (4), so that a transmission waveform "u'(t)" (see FIG. 7O ). When the waveform u'(t) is transmitted at a position of X=O, the waveform is changed to a waveform of FIG. 7D which is equivalent to the reference waveform u(t).

$$u(2d,t)=2Re\int_0^\infty U(\omega)e^{i(k(\omega)2d-\omega t)}d\omega \qquad \text{formula (2)}$$

$$k(\omega) = \frac{\omega}{c(\omega)} \qquad \text{formula (3)}$$

$$u'(t)=u(2d,t_{max}-t) \qquad \text{formula (4)}$$

In the above-described formulae, symbol "ω" shows an angular velocity, symbol "c(ω)" indicates a phase velocity of a guided wave, and symbol "$t_{max}$" is time determined based upon $t_{max}=2d/c_{min}$ when a minimum value of a group velocity is assumed as "$c_{min}$." It should be noted that the phase velocity "c(ω)" of the guided wave may be calculated by solving numeral value resolutions of the frequency equation which is described in "Ultrasonic Waves in Solid Media" written by J. L. Rose (see pages 159 to 162). A detailed content of this frequency equation is omitted.

The formed transmission waveform "u'(t)" is transferred to the guided wave transmitting/receiving means 3, and is displayed on the transmission waveform display window (see FIG. 5). As one display example, assuming now that the inspection region "R" is selected to be from 500 mm to 1500 mm, since a center of the inspection region "R" is equal to 1000 mm, a transmission waveform is calculated under such a condition that the distance d=1000 mm, and this calculated transmission waveform is displayed on the transmission waveform preview.

Next, transmitting/receiving operations of the guided wave are carried out (step S3). The transmitting/receiving operations of the guided wave are commenced by that the waveform forming/analyzing means 5 sends out a trigger signal to the guided wave transmitting/receiving means 3. The guided wave transmitting/receiving means 3 which has detected the trigger signal applies a transmission waveform to the guided wave transmitting/receiving element 1, and at the same time, transmits a trigger signal with respect to the A/D converter 4.

Since the guided wave transmitting/receiving element 1 to which the transmission waveform is applied is mechanically vibrated, this guided wave transmitting/receiving element 1 excites a guided wave 8 with respect to the pipe system 9. While the guided wave 8 is propagated through the pipe system 9 along an axial direction thereof, a component of this guided wave 8 which is reflected from a discontinuity point D(0) such as a crack and a reduced wall thickness is received by the guided wave transmitting/receiving element 1, and then, the received component is entered as a received waveform to the guided wave transmitting/receiving means 3. The guided wave transmitting/receiving means 3 amplifies the received waveform, and then sends the amplified received waveform to the AD converter 4.

The A/D converter 4 commences a digital converting operation of an analog reception signal in synchronism with the trigger signal which is generated at the same time when the guided wave transmitting/receiving means 3 applies the transmission waveform to the guided wave transmitting/receiving element 1. Thus, the amplified received waveform is converted into a digital signal by the A/D converter 4, and then, this digital signal is transferred to the waveform forming/analyzing means 5. Next, an inspection result is displayed as inspection information (step S4). In this case, the inspection result is displayed in the form of a waveform, assuming now that either time or a distance is expressed as an abscissa. When the above-described operation is ended, the pipe arrangement inspecting operation is accomplished.

Figure 8:
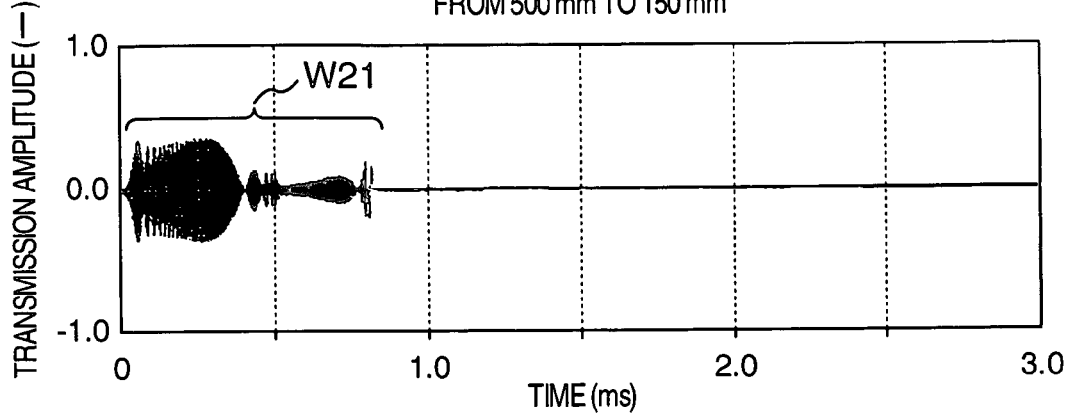
FIG. 8 is a diagram for indicating an example of a transmission waveform in the case that a guided wave is energized in such a manner that a duration time of a signal is reduced when reflection waveforms are received from a specific inspection region.
Figure 9A:
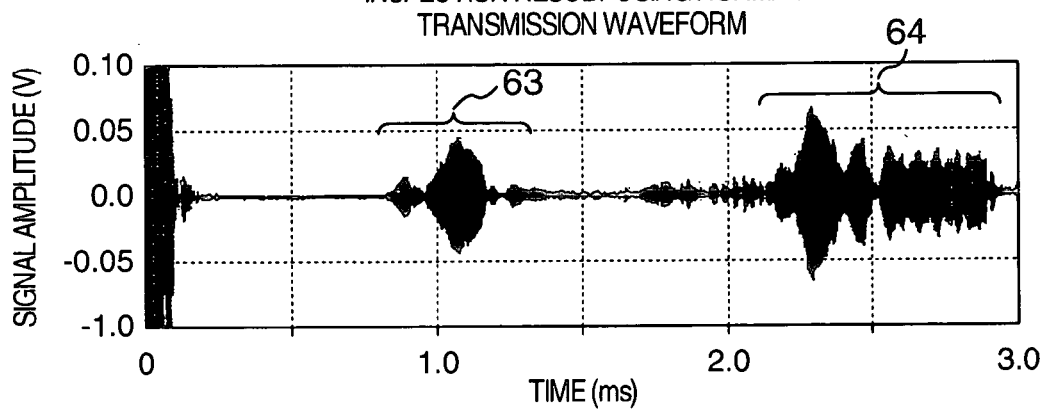
FIG. 9A and FIG. 9B are diagrams for representing results of tests capable of improving sensitivities with respect to defects located in a specific inspection region in the case that a guided wave is energized in such a manner that a duration time of a signal is reduced when reflection waveforms are received from the specific inspection region.
Figure 9B:
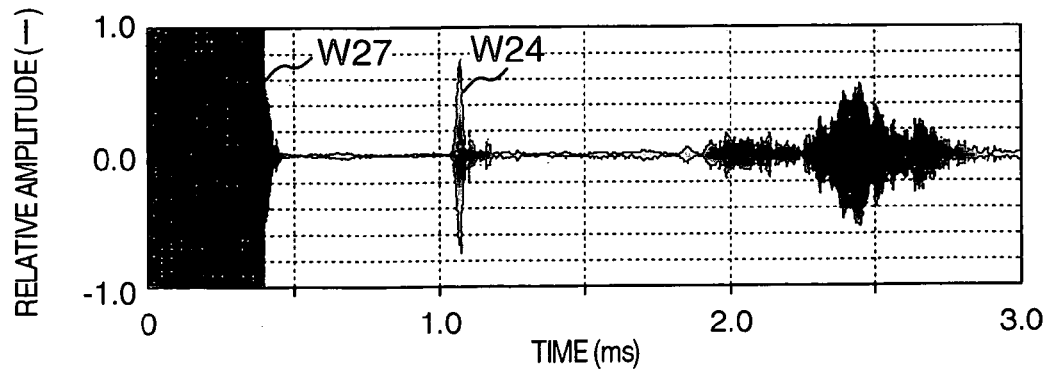

Next, referring now to FIG. 8 and FIG. 9A to FIG. 9B, a description is made of an example of test results obtained by that a pipe system having a defect is actually inspected by the pipe system inspecting apparatus according to the first embodiment of the present invention. It should be understood that the pipe system used in this test is the same as the pipe system previously described in the related art, namely a carbon steel pipe, the outer diameter of which is 114.3 mm, the pipe wall thickness of which is 6 mm, and the length of which is 5500 mm. The defect is made at a portion of this carbon steel pipe separated from an edge portion thereof by 1500 mm.

The guided wave transmitting/receiving element 1 was arranged at a position separated from the defect by 1000 mm (namely, separated from edge portion by 2500 mm), and was inspected by the pipe system inspecting apparatus according to this first embodiment. The following inspection conditions were entered via the inspection condition setting window: the pipe wall thickness of the pipe system was 6 mm; the material thereof was the carbon steel; and the inspection region was 500 mm to 1500 mm. Then, the following inspection conditions were entered via the reference waveform selecting/display window: the tone burst wave was selected; the cycle number was selected to be 4; and the center frequency was 500 KHz. At this time, a transmission waveform to be displayed on the transmission waveform display window is illustrated in FIG. 8. Also, an inspection result obtained as the inspection information is illustrated in FIG. 9B. The following fact could be confirmed. That is, a broadening trend of the waves on the time axis was suppressed in FIG. 9B, as compared with FIG. 9A, namely in the case that the normal transmission wave is employed.

Figure 27B:
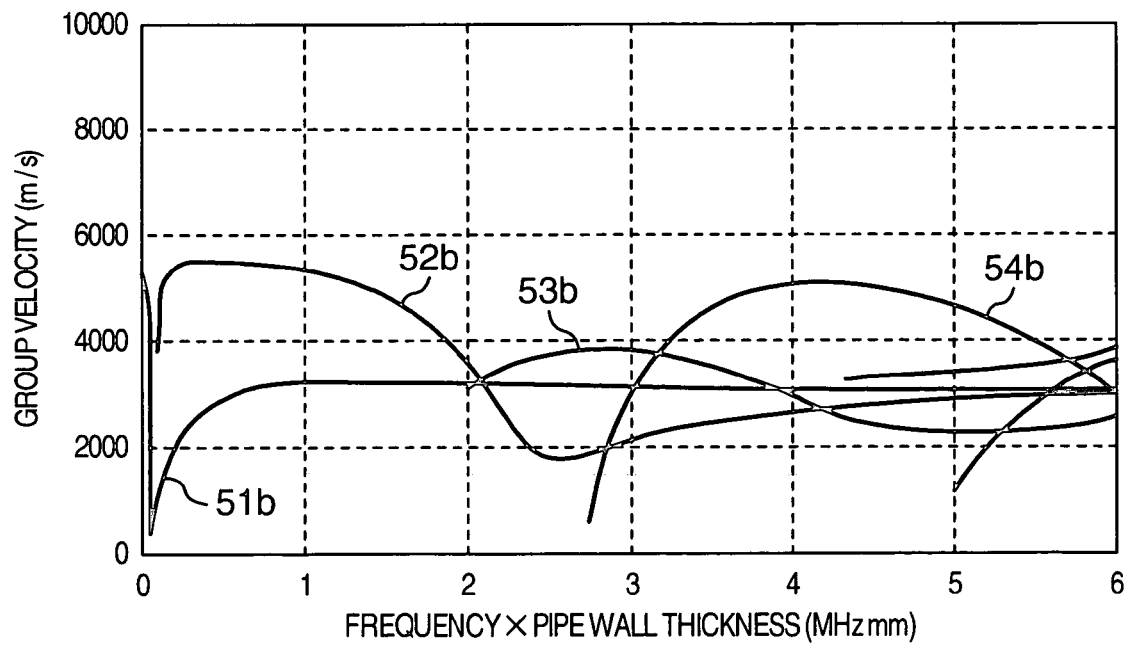
Figure 28:
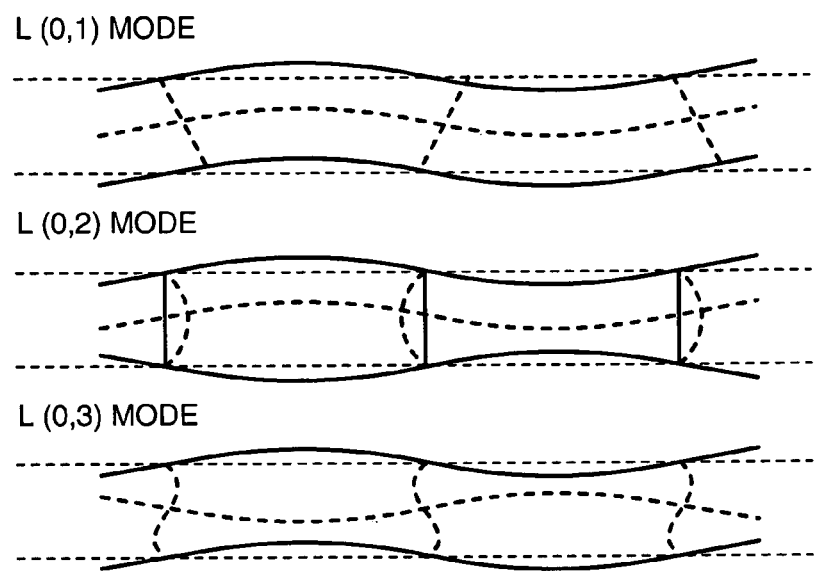
FIG. 28 is an explanatory diagram for illustratively explaining conditions of elastic deformation every vibration mode when the guided waves are propagated.

It should be understood that since broadening of the waveform (equivalent to "63" shown in FIG. 9A) on the time axis with employment of the normal transmission waveform is originally large in the region when the group velocity (51b of FIG. 27B) of the L(0, 1) mode and the group velocity (52b of FIG. 27B) of the L(0, 2) mode change largely by frequency, if this embodiment is applied, then such a waveform as W24 becomes. Accordingly, there is a very higher effect that broadening of the waveform on the time axis is suppressed. Concretely speaking, the pipe arrangement inspecting apparatus of this embodiment may be preferably employed in such a region defined by that frequency (MHz)×pipe wall thickness (mm) is selected from 0.5 to 4.0.

In accordance with the above-described pipe arrangement inspecting apparatus of the first embodiment, although the relatively higher frequency range where the sound velocity is dispersed is utilized, since lowering of the amplitude caused by the dispersion can be compensated at a specific position of the pipe arrangement, the detecting sensitivity of the defects located at the specific position of the pipe arrangement can be improved.

Next, as a second embodiment of the present invention, another embodiment will now be explained in which an inspection region is subdivided into a plurality of segments along an axial direction, and transmission waveforms are allocated to the respective segments so as to inspect these segments. Since a block diagram of an arrangement of a pipe arrangement inspecting apparatus according to this second embodiment is identical to the above-explained block diagram of the first embodiment, an explanation thereof is omitted.

Figure 10A:
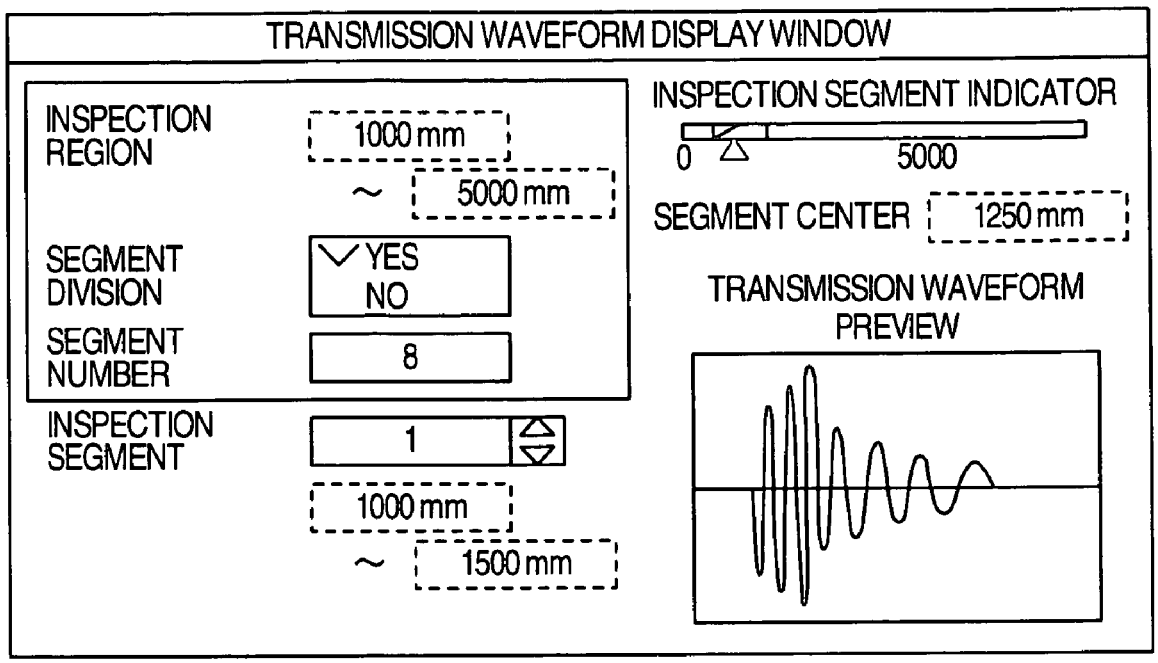
FIG. 10A and FIG. 10B illustratively show display examples of transmission waveform display windows used in a pipe arrangement inspecting apparatus according to a second embodiment of the present invention.
Figure 11:
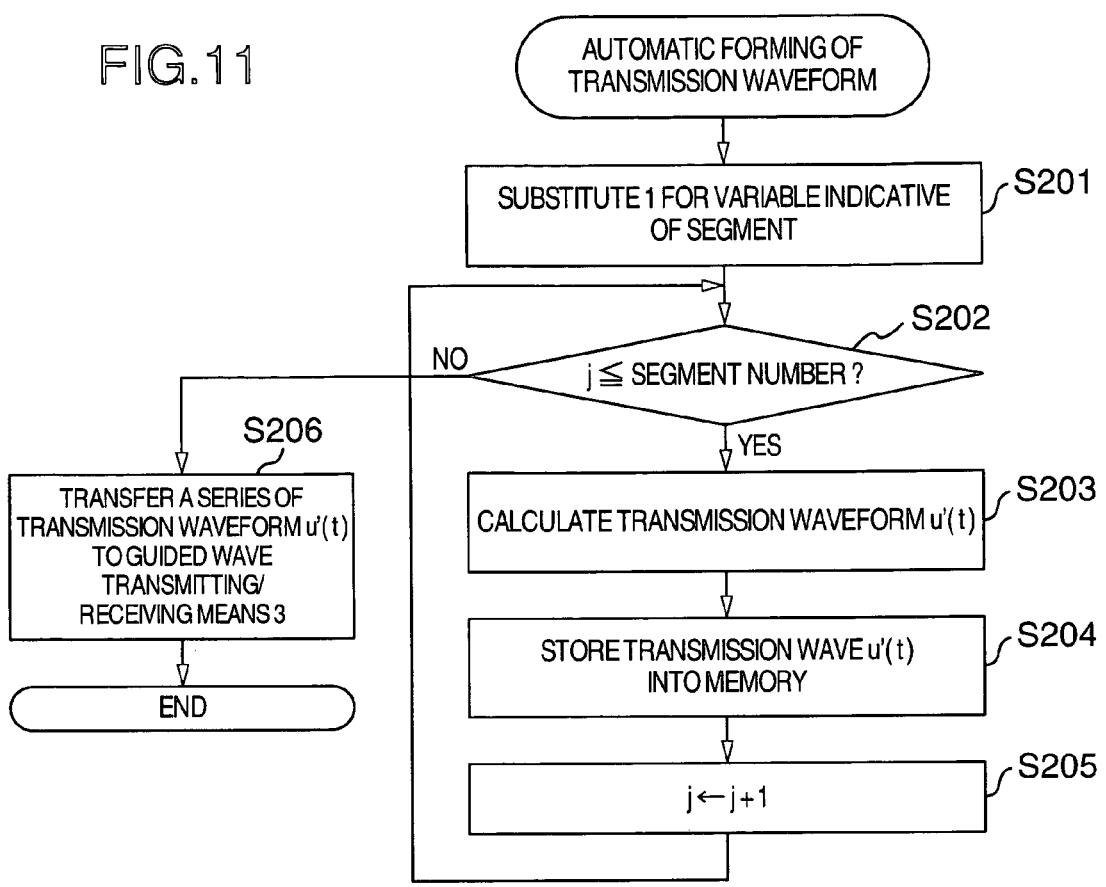
FIG. 11 is a flow chart for explaining an internal process operation executed by a waveform forming/analyzing means when a transmission waveform is automatically formed by the pipe arrangement inspecting apparatus according to the second embodiment of the present invention.
Figure 12:
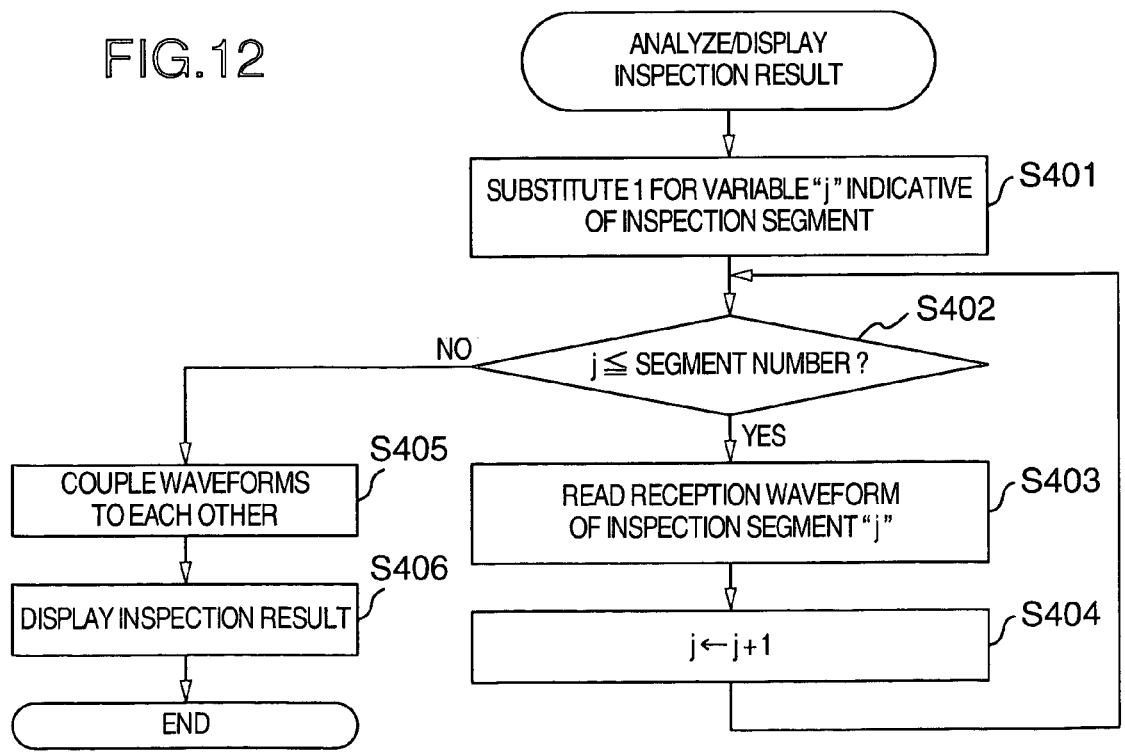
FIG. 12 is a flow chart for explaining an internal process operation executed by the waveform forming/analyzing means when an inspection result is analyzed/displayed by the pipe arrangement inspecting apparatus according to the second embodiment of the present invention.

Operations of the pipe arrangement inspecting apparatus according to the second embodiment of the present invention will now be described with reference to FIG. 10, FIGS. 13A–13D, and flow charts of FIG. 6, FIG. 11, and FIG. 12, which show internal process operations of the waveform forming/analyzing means 5. In the beginning, the waveform forming/analyzing means 5 requests the user to input an inspection condition (step S1). Although input operation at this time is similar to that of the first embodiment of the present invention, as indicated in the example of FIG. 10A, "YES" is selected in the segment subdivision on the transmission wave display window. At this time, while the division condition of the inspection segment is entered by a segment number, the waveform forming/analyzing means 5 determines the inspection segments in such a manner that lengths of the spective inspection segments may become equal to each other, and then allocates numbers to these inspection segments in this order from the smallest number as to the inspection segment located close to the guide wave transmitting/receiving element 1.

Figure 10B:
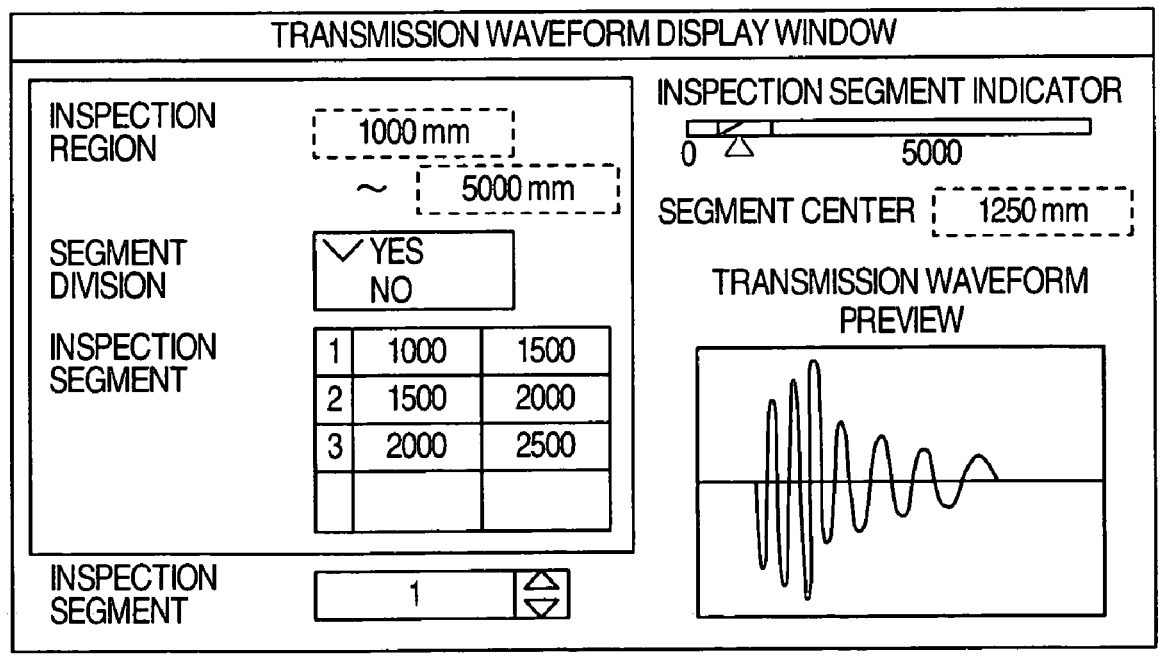

Alternatively, as shown in FIG. 10B, sections of inspection segments may be individually entered. When all of the conditions are inputted, the waveform forming/analyzing means 5 automatically forms a transmission waveform (step S2). A content of this process operation will now be explained with reference to the flow chart of FIG. 11. First of all, 1 is substituted for a variable "j" indicative of an inspection segment (step S201). Next, the waveform forming/analyzing means 5 judges as to whether or not the variable "j" is smaller than, or equal to the segment number (step S202). When j=1, since the waveform forming/analyzing means 5 judges "YES", the process operation is advanced to a step S203. To the contrary, when the wave forming/analyzing means 5 judges "NO", the process operation is advanced to a step S206. Next, the waveform forming/analyzing means 5 calculates a transmission waveform "u'(t)" based upon a reference waveform "u(t)", and a distance "d" measured from the guided wave transmitting/receiving element 1 up to a center of a j-th inspection segment (step S203). A content of this waveform calculation at this step is identical to that of the first embodiment of the present invention, an explanation thereof is omitted.

Next, the transmission waveform "u'(t)" is stored into a memory (step S204). Subsequently, 1 is added to the variable "j" (step S205). Next, the process operation is returned to the previous step S202. While the variable "j" is small than, or equal to the segment number, the waveform forming/analyzing means 5 repeatedly executes the process operations defined from the step S202 via the steps S203 and S204 to the step S205 so as to calculate the transmission waveforms "u'(t)" with respect to all of the inspection segments. In the case that the variable "j" exceeds the segment number, the waveform forming/analyzing means 5 transfers a series of the transmission waveforms "u'(t)" to the guided wave transmitting/receiving means 3 (step S206).

In the above-described step S206, the forming process operation of the transmission waveforms is accomplished.

All of the formed transmission waveforms are displayed on the transmission waveform display window (FIG. 10), so that these transmission waveforms can be confirmed. Next, the waveform forming/analyzing means 5 transmits and receives guided waves (step S3). This transmitting/receiving operation of the guided waves is identical to that of the first embodiment of the present invention. However, another step is additionally provided. That is, in this additional step, before the waveform forming/analyzing means 5 transmits a trigger signal to the guided wave transmitting/receiving means 3, this waveform forming/analyzing means 5 sends out a transmission waveform selecting signal, and selects a transmission signal.

Next, the waveform forming/analyzing means 5 analyzes an inspection result corresponding to the inspection information, and displays the analyzed inspection result (step S4) A content of this process operation will now be explained with reference to the flow chart shown in FIG. 12, and FIGS. 13A–13D. In the beginning, the waveform forming/analyzing means 5 substitutes 1 for a variable "j" indicative of an inspection segment (step S401). Next, the waveform forming/analyzing means 5 judges as to whether or not the variable "j" is smaller than, or equal to the segment number (step S402). When j=1, since the waveform forming/analyzing means 5 judges "YES", the process operation is advanced to a step S403. To the contrary, when the waveform forming/analyzing means 5 judges "NO", the process operation is advanced to a step S405. Next, the waveform forming/analyzing means 5 reads out a received waveform of the inspection segment "j" (step S403).

Next, the waveform forming/analyzing means 5 adds "1" to the variable "j" indicative of the inspection segment, and then, stores the added variable into the memory (step S404), and then, the process operation is advanced to the step S402. While the variable "j" is smaller than, or equal to the segment number, the waveform forming/analyzing means 5 repeatedly executes the process operations defined from the step S402 via the step S403 to the step S404 so as to read out received waveforms with respect to all of the inspection segments. In the case that the variable "j" exceeds the segment number, the waveform forming/analyzing means 5 provides time gates corresponding to the positions of the inspection segments with respect to the read received waveforms, and extracts signals within each of the time gates, and then couples these extracted signals to each other on the time axis (step S405).

Next, the waveform forming/analyzing means 5 outputs such a waveform whose time, or distance is defined as an abscissa to the display means 7 as a picture signal, and thus, the display means 7 receives the picture signal so as to display thereon the waveform (step S406). FIGS. 13A–13D indicate an example of a display content. In this drawing, FIG. 13B represents a received waveform when a transmission waveform which becomes a high sensitivity with respect to a second inspection segment "R2" is applied to the guided wave transmitting/receiving element 1. In FIG. 13B, reference numeral 21 shows a transmission waveform, reference numeral 22 indicates a reflection waveform reflected from a defect located in the second inspection segment R2, reference numeral 23 represents a reflection waveform reflected from a third inspection segment R3, and symbol "G2" is a gate corresponding to the second inspection segment R2.

Also, FIG. 13C shows a received waveform when a transmission waveform which becomes a high sensitivity with respect to the third inspection segment "R3" is applied to the guided wave transmitting/receiving element 1. In FIG. 13C, reference numeral 24 shows a transmission waveform, reference numeral 25 indicates a reflection waveform reflected from a defect located in the second inspection segment R2, reference numeral 26 represents a reflection waveform reflected from the third inspection segment R3, and symbol "G3" is a gate corresponding to the third inspection segment R3. FIG. 13D shows a coupled waveform made by coupling the waveforms to each other, which are located in the respective gates G2 and G3. Since the waveforms whose sensitivities are high within the gates are coupled to each other, such waveforms having high sensitivities can be obtained with respect to all of the inspection segments.

Figure 14A:
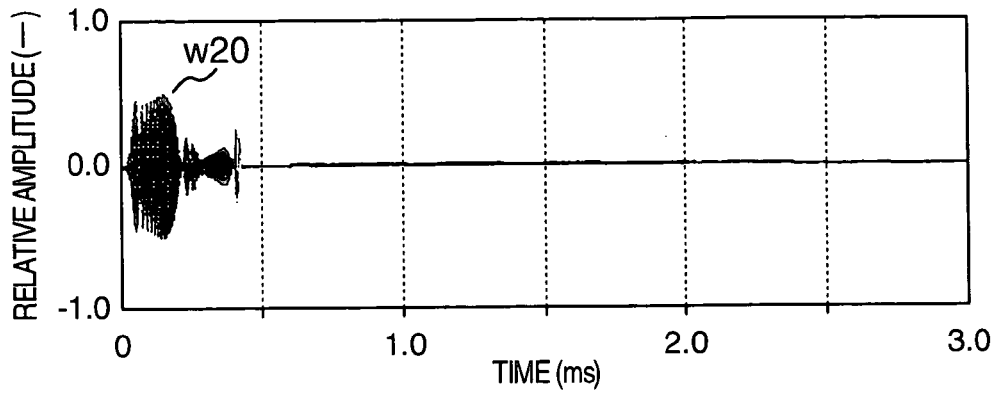
FIG. 14A to FIG. 14C are diagrams for indicating an example of transmission waveforms in the case that a guided wave is energized in such a manner that a duration time of a signal is reduced when reflection waveforms reflected from a specific inspection segment are received.
Figure 14B:
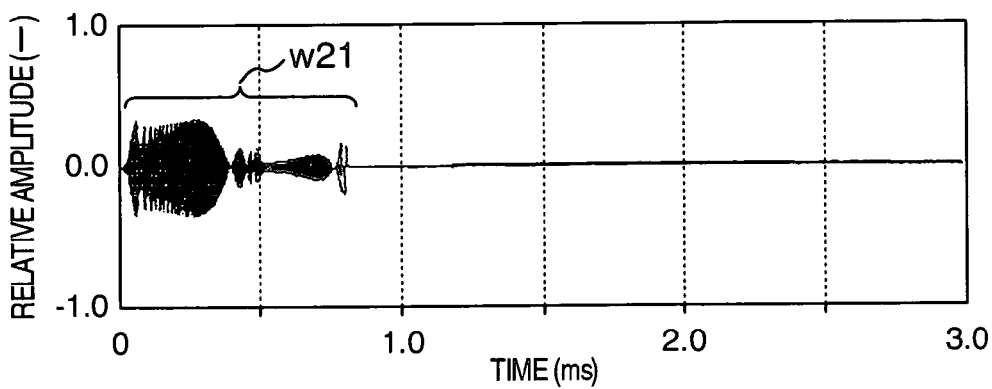
Figure 14C:
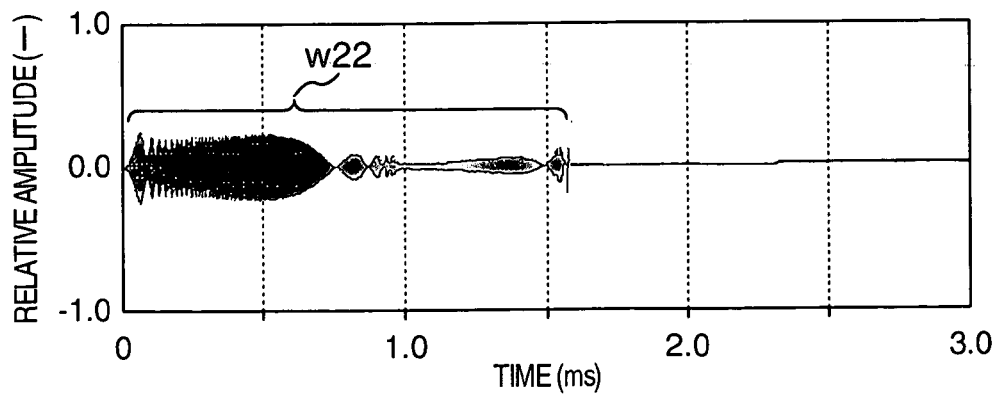
Figure 26:
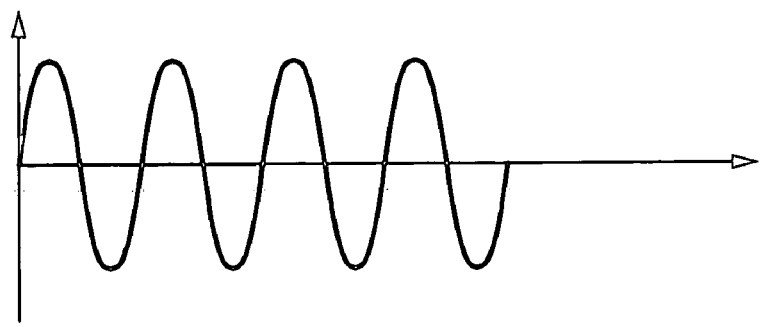
FIG. 26 is an explanatory diagram for explaining a tone burst wave corresponding to an example of a waveform which is applied to a guided wave transmitting/receiving element.

FIG. 14A to FIG. 14C show an example of transmission waveforms formed by the pipe arrangement inspecting apparatus according to the second embodiment of the present invention. At this time, a reference waveform is equal to a tone burst wave having a frequency of 500 KHz and the same waveform as that of FIG. 26, which is given by the following formula (5):

$$u(t) = \begin{cases} \sin(\omega t) & 0 \le t \le 8(\mu s) \\ 0 & t < 0, t > 8(\mu s) \end{cases} \qquad \text{formula (5)}$$

A transmission waveform "W20" shown in FIG. 14A corresponds to a transmission waveform which is calculated based upon the above-described formula (4) by setting d=500 mm. In other words, W20 is obtained in such a manner that when a guided wave transmitted from the guided wave transmitting/receiving element 1 is reflected from a defect located at a position separated by 500 mm from this guided wave transmitting/receiving element 1, and then is again received by the guided wave transmitting/receiving element 1, this transmission wave W20 is calculated by referring to the data of the phase velocity (52a shown in FIG. 27A) in order that a duration time of the guided wave may become a short duration time. Another transmission waveform calculated under condition of d=1000 mm is represented as a transmission waveform "W21" of FIG. 14B, and a further transmission waveform calculated under condition of D=2000 mm is indicated as a transmission waveform "W22" of FIG. 14C.

Next, a description is made of effects achieved in such a case that guided waves are energized by the transmission waveforms produced in the pipe arrangement inspecting apparatus according to the second embodiment of the present invention with reference to FIGS. 15A–15C. While the distance "d" between the guided wave transmitting/receiving element 1 was varied, reflection waves were acquired. The acquision result is shown in FIG. 15. FIG. 15A indicates such a result that while the reference waveform was the tone burst having the frequency of 500 KHz in 4 cycles and such a transmission wave "u'(t)" calculated under d=500 mm was employed, reflection waves reflected from a deflect located at a forward position separated by 500 mm from the guided wave transmitting/receiving element 1 were acquired.

Figure 29A:
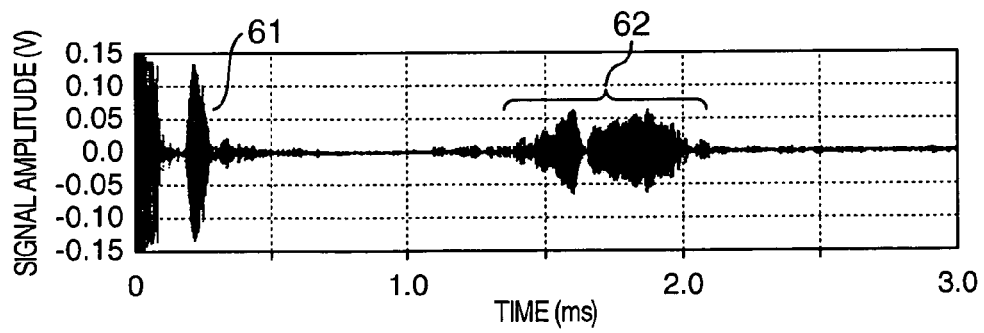
FIG. 29A and FIG. 29B are explanatory diagrams for explaining that both the amplitudes of the reflection waveforms and the duration times are varied, depending upon distances, when the pipe arrangement having the outer diameter of 114.3 mm and the pipe wall thickness of 6 mm, to which the defects are applied, is inspected by using the guided wave in the L(0, 2) mode, which is driven by such a tone burst wave having a frequency of 500 KHz for 4 cycles.
Figure 29B:
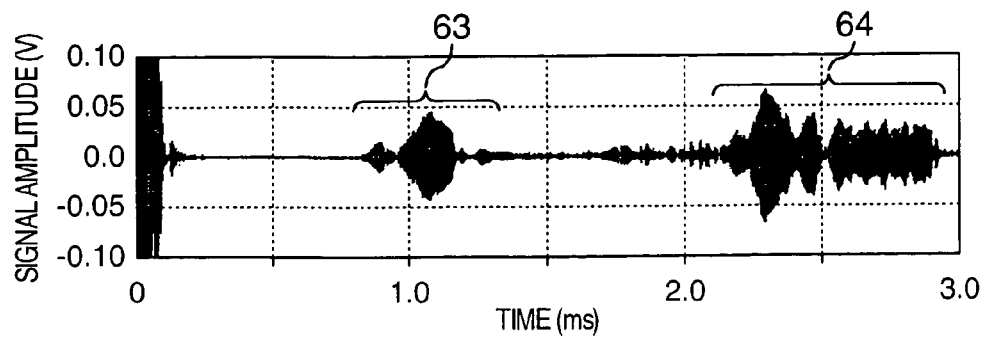

FIG. 15B indicates a result obtained as follows: That is, while such a transmission waveform "u'(t)" calculated under d=1000 mm was employed, reflection waves reflected from a defect located at a forward position separated by 1000 mm from the guided wave transmitting/receiving element 1 were acquired. FIG. 15C indicates a result obtained as follows: That is, while such a transmission waveform "u'(t)" calculated under d=2000 mm was employed, reflection waves reflected from a defect located at a forward position separated by 2000 mm from the guided wave transmitting/receiving element 1 were acquired. Symbols "W23", "W24", and "W25" represent reflection waves which are reflected from the defects. When any of these reflection wave signals W23, W24, W25 are compared with the reflection waveforms "61" and "63" shown in FIGS. 29A–29B, duration times thereof are shorter than those of the reflection waveforms "61" and "63." It should also be understood that symbols "W26", "27", "W28" show transmission waveforms.

Figure 16:
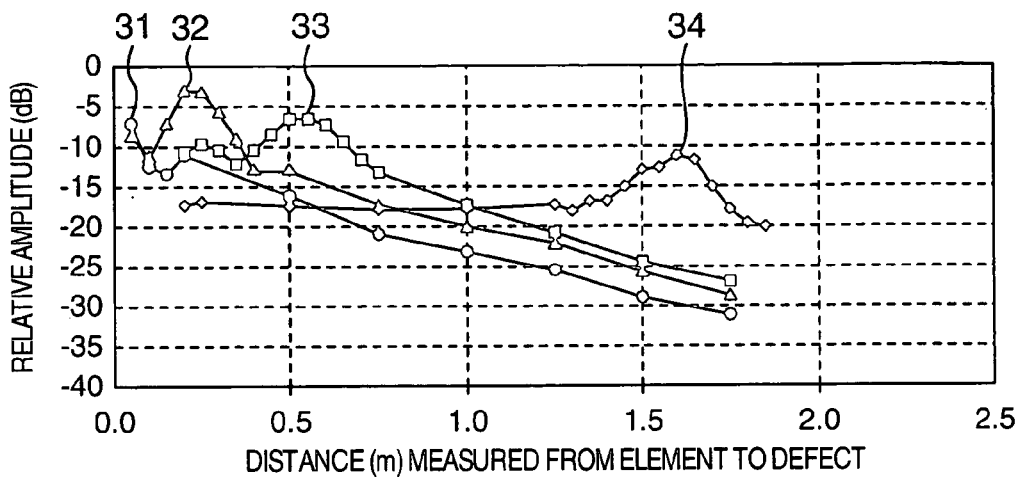
FIG. 16 is a diagram for indicating an example of signals when guided waves are received which are reflected from a reflection source located at a specific distance in such a case that a guided wave is energized in such a manner that lowering of an amplitude caused by dispersion at the specific distance is compensated.

FIG. 16 shows a test result obtained by measuring a relationship between distances defined from the guided wave transmitting/receiving element 1 up to the defects, and amplitudes of received waveforms. In this drawing, a test result "31" is such a case that a transmission waveform (equal to reference waveform) is employed which is calculated under d=0 mm; a test result "32" is such a case that a transmission waveform is employed which is calculated under d=250 mm; a test result "33" is such a case that a transmission waveform is employed which is calculated under d=500 mm; and a test result "34" is such a case that a transmission waveform is employed which is calculated under d=1500 mm. As to any of these test results, the following fact can be understood. That is, in such a distance that the duration time of the guided wave becomes a short duration time, a relative amplitude indicates a maximum turning value, and a sensitivity with respect to the defects becomes high. Difference between the measurement result 31 and other measurement results correspond to improved components which are obtained by employing the transmission method established based upon this second embodiment.

In accordance with the above-described pipe arrangement inspecting apparatus of the second embodiment of the present invention, while the pipe arrangement explained in the second embodiment of the present invention is subdivided into a plurality of the inspection segments along the axial direction, the received signals are coupled to each other, which are acquired by transmitting/receiving the transmission signals. These transmission signals are different from each other every subdivided inspection segment. As a consequence, all of the positions located in the pipe arrangement can be inspected in the higher sensitivities.

Figure 17A:
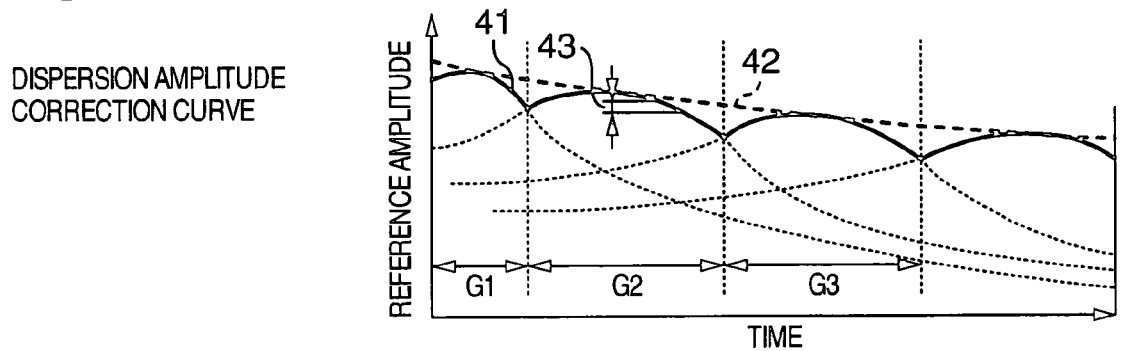
FIG. 17A to FIG. 17C are explanatory diagrams for explaining a method for correcting amplitudes of received waveforms, depending upon distances measured from a guide wave transmitting/receiving element in a pipe arrangement inspecting apparatus according to a third embodiment of the present invention.

Next, a pipe arrangement inspecting apparatus according to a third embodiment of the present invention will now be explained by referring to FIGS. 17A–17C. Since an apparatus arrangement of the third embodiment is identical to the apparatus arrangements according to the first and second embodiments, explanations thereof are omitted. Although inspecting operations of the pipe arrangement inspecting apparatus according to this third embodiment are substantially equivalent to that of the second embodiment of the present invention, the below-mentioned function is additionally provided subsequent to the step S405 in the process operation for analyzing/displaying the inspection result (see FIG. 12). In other words, the waveform forming/analyzing means 5 corrects a received waveform in such a way that a dispersion amplitude correction curve 41 of which received waveform is shown in FIG. 17A is lowered with respect to an envelope line 42 thereof, and then, newly defines the corrected waveform as a received waveform.

Figure 17B:
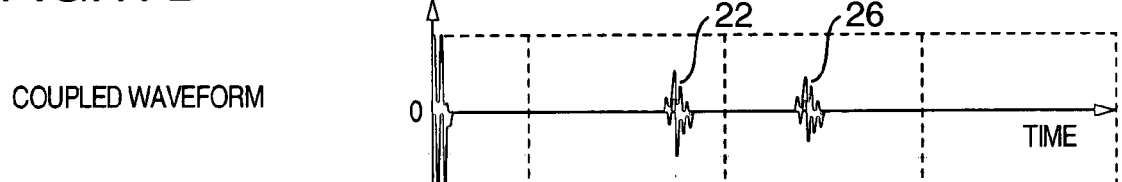
Figure 17C:
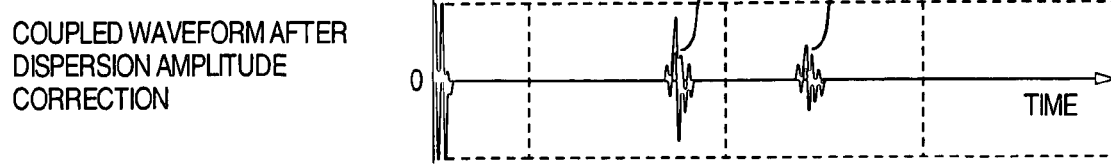

For example, assuming now that a waveform of FIG. 17B corresponds to a coupled waveform of received waveforms, the waveform forming/analyzing means 5 corrects an amplitude difference 43 with respect to a waveform 22. Since the amplitude difference 43 is corrected, a coupled waveform after the dispersion amplitude correction becomes such a coupled waveform as shown in FIG. 17C. As indicated in this drawing, the waveform 22 is represented as such a waveform 22a whose amplitude is corrected. It should be noted that this dispersion amplitude correction curve 41 is formed from the data acquired based upon the test of FIG. 16.

In accordance with the above-described pipe arrangement inspecting apparatus of the third embodiment of the present invention, there is such an effect that deteriorations of the detecting performance occurred at a specific position can be suppressed by correcting such a phenomenon that the signal level is lowered at the position deviated from the center of the inspection segment.

Next, a pipe arrangement inspecting apparatus according to a fourth embodiment of the present invention will now be described with reference to FIG. 18 to FIG. 24.

Figure 18:
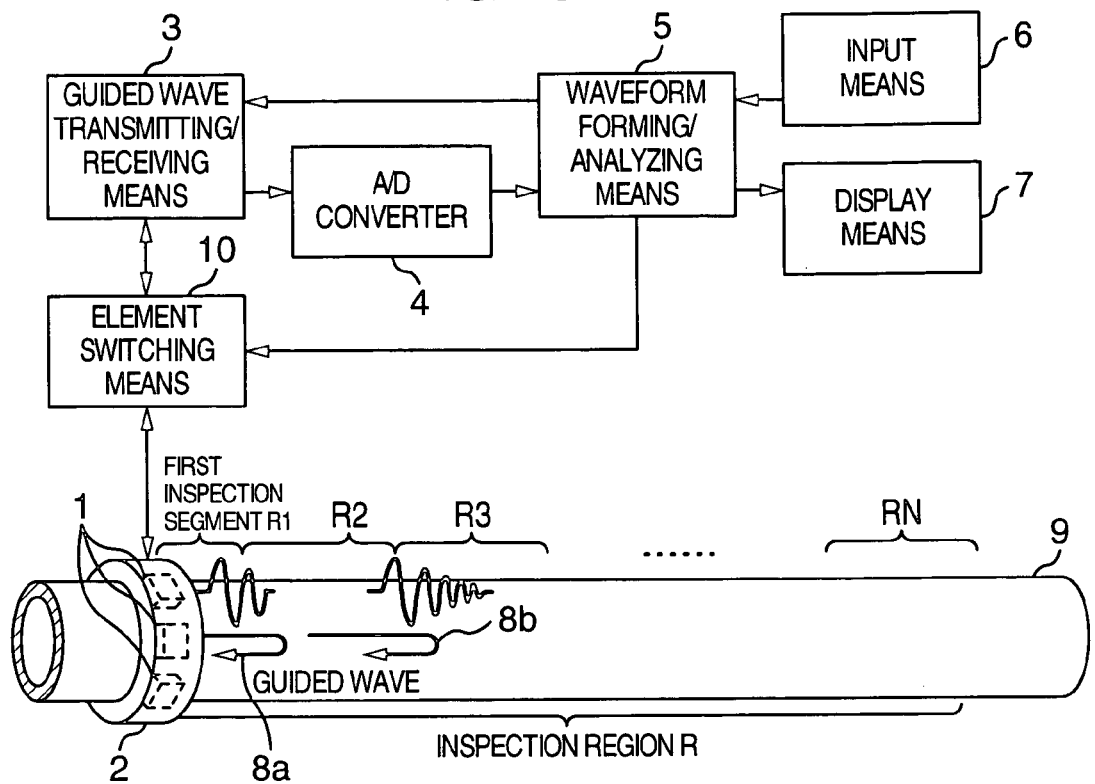
FIG. 18 is a schematic block diagram for showing an arrangement of a pipe arrangement inspecting apparatus according to a fourth embodiment of the present invention.

FIG. 18 is a schematic block diagrams for explaining an arrangement of a pipe arrangement inspecting apparatus according to this fourth embodiment. In this drawing, reference numeral 1 shows a guided wave transmitting/receiving element; reference numeral 2 indicates a transmitting/receiving element ring; reference numeral 3 represents a guided wave transmitting/receiving means; reference numeral 4 denotes an A/D converter; reference numeral 5 is a waveform forming/analyzing means; reference numeral 6 shows an input means; reference numeral 7 indicates a display means; and reference numeral 10 shows an element switching means.

The element switching means 10 corresponds to such a means which is controlled in response to a control signal supplied from the waveform forming/analyzing means 5 so as to select the guided wave transmitting/receiving element 1 to be connected to the guide wave transmitting/receiving means 3. This element switching means 10 is constructed by employing, for example, a commercially available multiplexer. Since other arrangements of this pipe arrangement inspecting apparatus are similar to those of the first embodiment of the present invention, explanations thereof are omitted.

Figure 19:
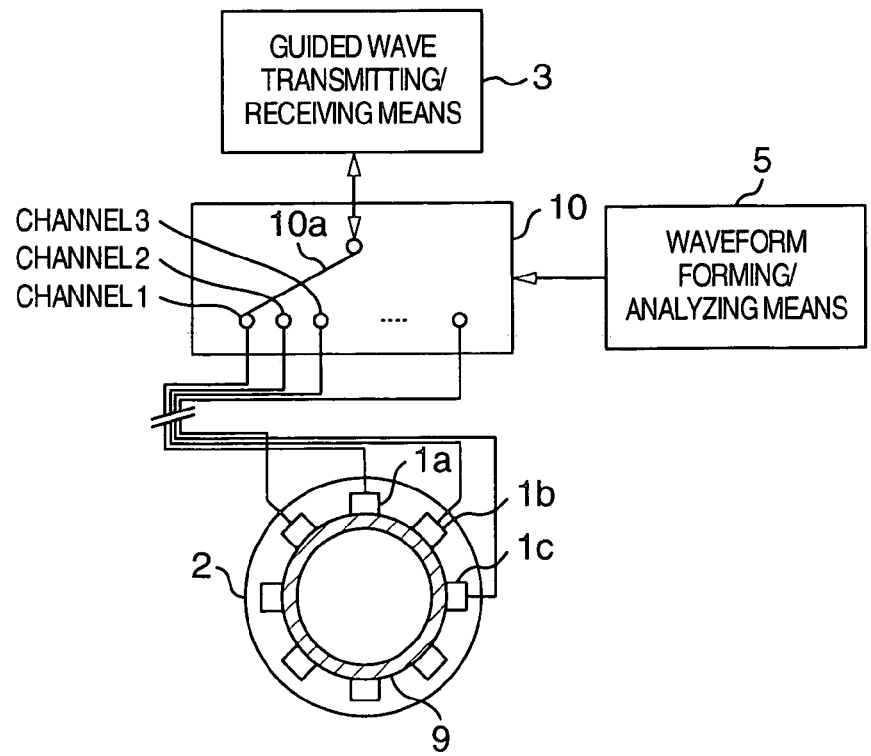
FIG. 19 is a connection diagram between an element switching means and a guided wave transmitting/receiving element in the pipe arrangement inspecting apparatus of the fourth embodiment.

FIG. 19 is a connection diagram between the element switching means 10 and the guided wave transmitting/receiving elements 1. In this drawing, reference numerals "1a", "1b", and "1c" represent guided wave transmitting/receiving elements. These guided wave transmitting/receiving elements 1a, 1b, 1c are connected a channel 1, a channel 2, and a channel 3 of the element switching means 10. Although connection lines of a channel 4 and succeeding channels are omitted in FIG. 10, these channels are similarly connected to other guided wave transmitting/receiving elements in an one-to-one corresponding relationship.

Figure 20:
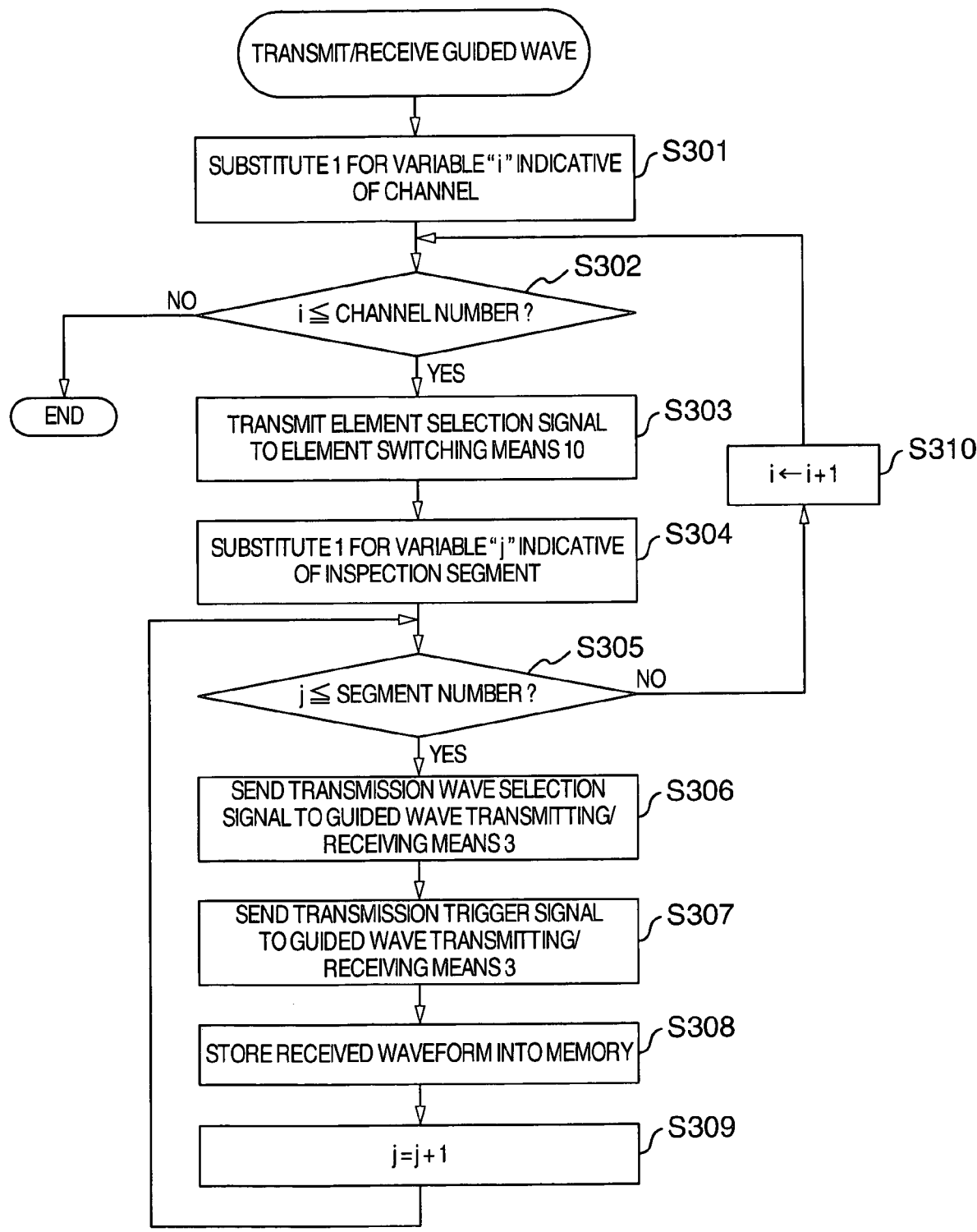
FIG. 20 is a flow chart for describing an internal process operation executed in a waveform forming/analyzing means when a guided wave is transmitted/received in the pipe arrangement inspecting apparatus according to the fourth embodiment.
Figure 21:
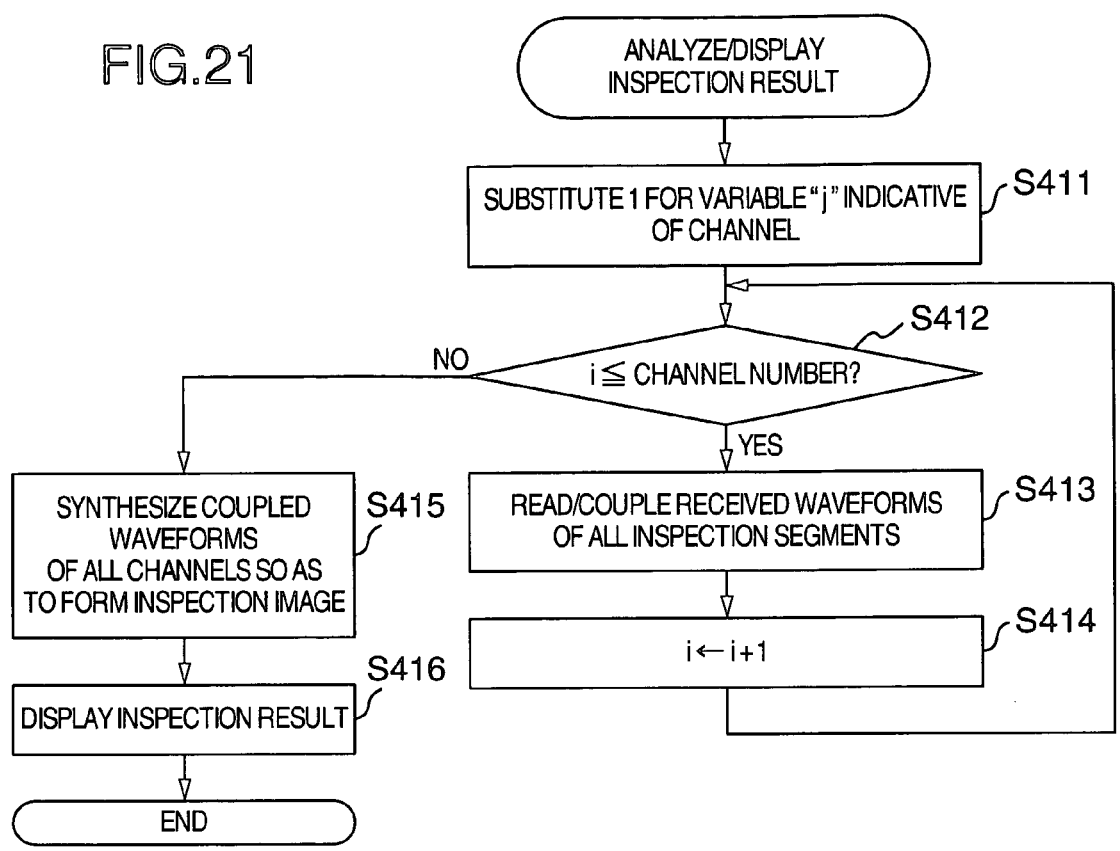
FIG. 21 is a flow chart for describing an internal process operation executed in a waveform forming/analyzing means when an inspection result is analyzed/displayed in the pipe arrangement inspecting apparatus according to the fourth embodiment.
Figure 22A:
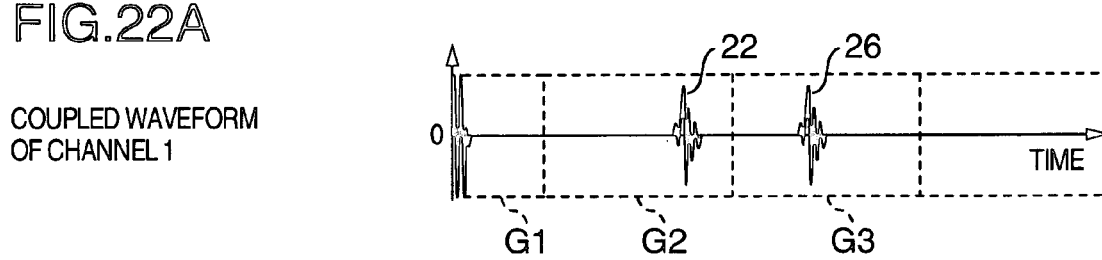
FIG. 22A and FIG. 22B are explanatory diagrams for explaining steps in which received waveforms are synthesized with each other so as to obtain a synthesized picture in the pipe arrangement inspecting apparatus of the fourth embodiment.

Next, inspecting operations of the pipe arrangement inspecting apparatus according to this fourth embodiment of the present invention will now be described with reference to flow charts shown in FIG. 6, FIG. 20, FIG. 21, and a waveform diagram of FIG. 22. First, the waveform forming/analyzing means 5 requests a user to input an inspection condition (step S1). Since the operation executed in this step S1 is identical to that of the second embodiment of the present invention, explanations thereof are omitted. Next, the waveform forming/analyzing means 5 automatically forms a transmission waveform (step S2). Since operation executed in this step S2 is identical to that of the second embodiment of the present invention, explanations thereof are omitted.

Next, the guided wave transmitting/receiving means 3 transmits/receives guided waves (step S3). A content of this process operation will now be explained with reference to FIG. 20. First of all, the waveform forming/analyzing means 5 substitutes 1 for a variable "i" which indicates a channel and has been stored in a memory (step S301). Next, the waveform forming/analyzing means 5 judges as to whether or not the variable "i" is smaller than, or equal to a channel number (step S302). Since the waveform forming/analyzing means 5 judges "YES" when i=1, the process operation is advanced to a step S303. To the contrary, when the waveform forming/analyzing means 5 judge "NO" at this time, the process operation is ended. In the step S303, the waveform forming/analyzing means 5 sends out an element selecting signal to the element switching means 10 (step S303).

The element switching means 10 which receives the element selecting signal switches the switch 10a so as to electrically connect the guided wave transmitting/receiving means 3 to the channel 1. As a result, the guided wave transmitting/receiving means 3 is electrically connected to the guided wave transmitting/receiving element 1a. Next, the waveform forming/analyzing means 5 substitutes 1 for a variable "j" which indicates an inspection segment and has been stored in the memory (step S304). Next, the waveform forming/analyzing means 5 judges as to whether or not the variable "j" is smaller than, or equal to an inspection segment number (step S305). Since the waveform forming/analyzing means 5 judges "YES" when j=1, the process operation is advanced to a step S306. To the contrary, when the waveform forming/analyzing means 5 judge "NO" at this time, the process operation is advanced to a step S310 (step S305).

Next, the waveform forming/analyzing means 5 transmits a transmission wave selecting signal to the guided wave transmitting/receiving means 3 in order that this guided wave transmitting/receiving means 3 prepares the transmission waveform which has been formed with respect to the first inspection segment R1 (step S306). Next, the waveform forming/analyzing means 5 transmits a trigger signal for a transmission operation with respect to the guided wave transmitting/receiving means 3 (step S307). The guided wave transmitting/receiving means 3 which has detected this trigger signal applies a transmission waveform via the element switching means 10 to the guided wave transmitting/receiving element 1a, and at the same time, transmits the trigger signal with respect to the A/D converter 4. Since the guided wave transmitting/receiving element 1a to which the transmission waveform is applied is mechanically vibrated, this guided wave transmitting/receiving element 1a excites a guided wave 8a with respect to the pipe arrangement 9.

While the guided wave 8a is propagated through the pipe arrangement 9 along an axial direction thereof, a guided wave 8a which is reflected from a discontinued point such as a crack and a reduced wall thickness is received by the guided wave transmitting/receiving element 1a, and then, the received component is entered as a received waveform to the guided wave transmitting/receiving means 3. The guided wave transmitting/receiving means 3 amplifies the received waveform, and then sends the amplified received waveform to the A/D converter 4. The A/D converter 4 commences a digital converting operation of an analog reception signal in synchronism with the trigger signal which is generated at the same time when the guided wave transmitting/receiving means 3 applies the transmission waveform to the guided wave transmitting/receiving element 1a. Thus, the amplified received waveform is converted into a digital signal by the A/D converter 4, and then, this digital signal is transferred to the waveform forming/analyzing means 5.

Next, the waveform forming/analyzing means 5 stores the digital signal into a memory (step S308). Next, the waveform forming/analyzing means 5 adds "1" to the variable "j" indicative of the inspection segment, and then, stores the added variable into the memory (step S309), and then, the process operation is advanced to the step S305. While the variable "j" is smaller than, or equal to the inspection segment number, the waveform forming/analyzing means 5 repeatedly executes the process operations defined from the step S305 via the steps S306, S307, S308 to the step S309, and transmits guided waves based upon the transmission waveforms which have been formed every inspection segment with respect to a plurality of inspection segments along the axial direction of the pipe arrangement 9, and then, stores all of received waveforms as digital signals into the memory. In the case that the variable "j" exceeds the segment number, the waveform forming/analyzing means 5 adds 1 to the variable "i" (step S310).

Next, the waveform forming/analyzing means 5 judges as to whether or not the variable "i" is smaller than, or equal to the channel number. While the variable "i" is smaller than, or equal to the channel number, the waveform forming/analyzing means 5 repeatedly carries out such a process operation defined from the step S302 via the steps S303, S304, and the repetition loop (defined from steps S305 to S309) up to the step S310, and also executes the repetition loop defined from the step S305 to the step S309 with respect to all of the guided wave transmitting/receiving elements which are arrayed along the circumferential direction of the pipe arrangement 9. When the variable "i" exceeds the inspection segment number, the process operation is ended.

Next, an inspection result corresponding to the inspection information is analyzed/displayed (step S4). A content of this process operation will now be explained with reference to FIG. 21. First of all, the waveform forming/analyzing means 5 substitutes 1 for a variable "i" which indicates a channel number and has been stored in a memory (step S411). Next, the waveform forming/analyzing means 5 judges a to whether or not the variable "i" is smaller than, or equal to the channel number (step S412). Since the waveform forming/analyzing means 5 judges "YES" when i=1, the process operation is advanced to a step S413. To the contrary, when the waveform forming/analyzing means 5 judge "NO" at this time, the process operation is advanced to a step S415.

Next, the waveform forming/analyzing means 5 reads out received waveforms of all of the inspection segments which have been acquired in the channel "i", and then couples these read received waveforms to each other (step S413). A content of this process operation is equal to such a process operation that the process operation defined at the step S406 is eliminated from the analyzing/displaying process operation (FIG. 12) of the inspection result, corresponding to the inspection information, in the second embodiment of the present invention, so that explanations thereof are omitted.

Next, the waveform forming/analyzing means 5 adds 1 to the variable "j" indicative of the inspection segment, and then stores the added variable "j" into the memory, and then, the process operation is advanced to a step S412 (step S414). When the variable "j" is smaller than, or equal to the inspection segment number, since the waveform forming/analyzing means 5 repeatedly executes the process operation defined from the step S412 via the step S413 to the step S414, this waveform forming/analyzing means 5 reads out the received waveforms of all of the segments for all of the channels, and then couples these read received waveforms to each other. When the variable "i" exceeds the channel number in the step S412, the waveform forming/analyzing means 5 forms information of an inspected image in which the circumferential direction of the pipe arrangement is expanded to a plane by employing the coupled waveforms of all of the channels (step S415). Since the steps for forming the information of this inspected image is identical to the picture processing operation of the B scope (namely, B-mode scope) executed in the normal ultrasonic inspecting operation, detailed contents thereof are omitted.

Figure 22B:
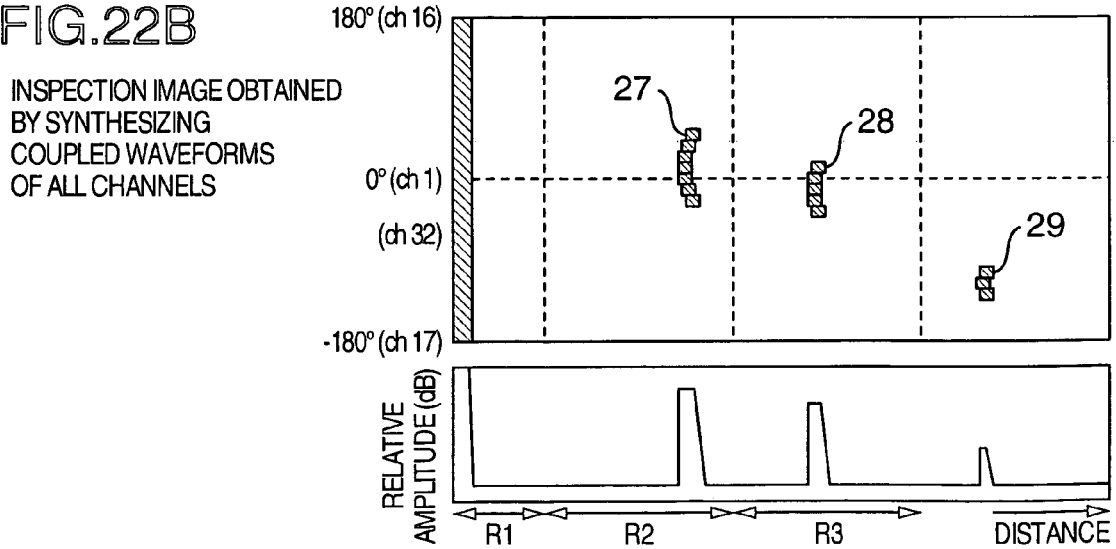

Next, the waveform forming/analyzing means outputs the picture signal of the information as to the inspected image to the display means 7, and then, the display means 7 receives the picture signal to display such an inspected image as represented in FIG. 22B (step S416).

Figure 23A:
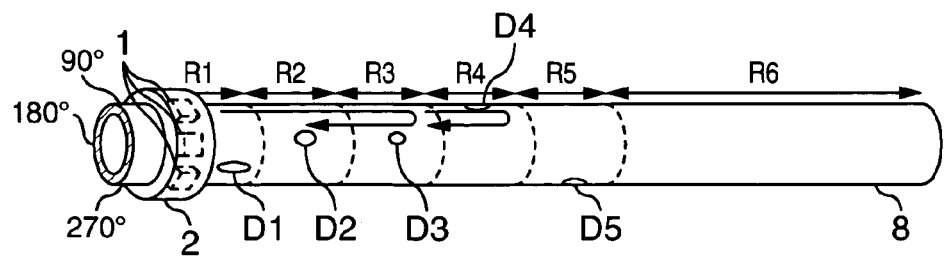
FIG. 23A and FIG. 23B are explanatory diagrams for explaining that positions of reflection waveforms are displayed on a plane where a pipe arrangement is extended when a pipe arrangement having an outer diameter of 114.3 mm and a pipe wall thickness of 6 mm, to which a defect has been applied, is inspected by such a guided wave in an L(0, 2) mode and having a center frequency of 500 KHz by employing the pipe arrangement inspecting apparatus of the fourth embodiment.

An example of results obtained by inspecting a pipe arrangement containing a defect by using the pipe arrangement inspecting apparatus according to the fourth embodiment of the present invention will now be explained with reference to FIG. 23 and FIG. 24. FIG. 23A schematically indicates an inspection system in which 32 pieces of the guided wave transmitting/receiving elements 1 are arranged at a position separated from the edge portion of the pipe arrangement 9 by 100 mm along the circumferential direction thereof, while this pipe arrangement 9 has an outer diameter of 114 mm, a thickness of 6 mm, and a length of 5500 mm. These guided wave transmitting/receiving elements 1 are gripped by the transmitting/receiving element rings 2.

In this drawing, symbols "D1", "D2", "D4", "D5" show truncated-cone-shaped defects whose thicknesses have been reduced. That is to say, symbol "D1" corresponds to a defect whose thickness has been reduced by 80% (4.8 mm) in maximum; symbol "D2" corresponds to a defect whose thickness has been reduced by 50% (3.0 mm) in maximum; symbol "D4" corresponds to a defect whose thickness has been reduced by 40% (2.4 mm) in maximum; and symbol "D5" corresponds to a defect whose thickness has been reduced by 20% (1.2 mm) in maximum. Also, symbol "D3" corresponds to a drill through-hole having a diameter of 4 mm.

Figure 23B:
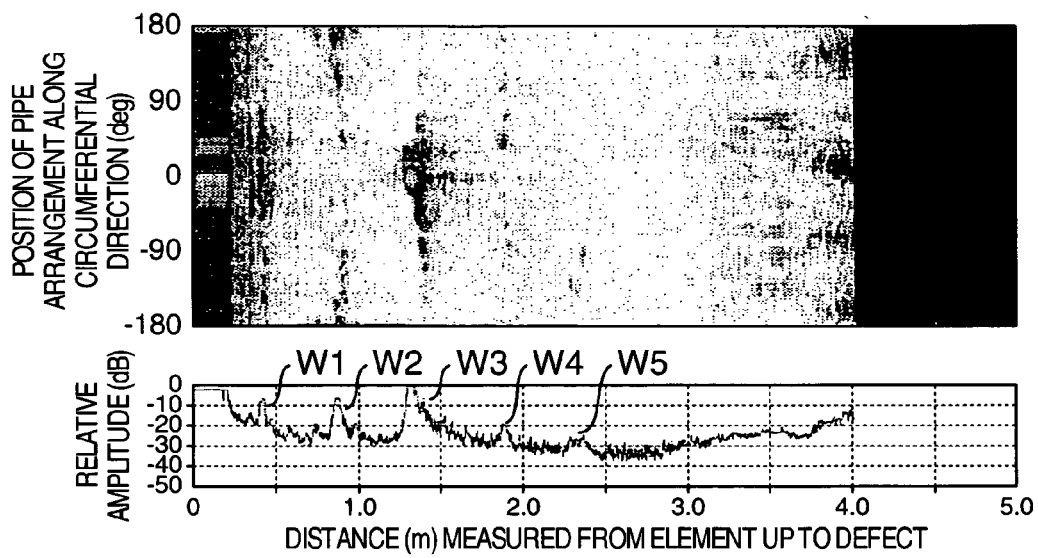

The positions of the respective defects along the circumferential direction are determined as follows: The position of the defect "D1" corresponds to 0°; the position of the defect "D2" corresponds to 180°; the position of the defect "D4" corresponds to 90°; and the position of the defect "D5" corresponds to -90°. Symbols "R1", "R2", "R3", "R4", "R5", and "R6" represent inspection segments. That is to say, the inspection segment "R1" is defined from 0 to 250 mm; the inspection segment "R2" is defined from 250 mm to 750 mm; the inspection segment "R3" is defined from 750 mm to 1250 mm; the inspection segment "R4" is defined from 1250 to 1750 mm; the inspection segment "R5" is defined from 1750 mm to 2250 mm; and the inspection segment "R6" is defined from 2250 mm to 5500 mm. The reference waveform used to produce the transmission waveform is a tone burst wave having a frequency of 500 KHz for 4 cycles. FIG. 23B represents an inspection result (namely, synthesized image of all channels). As indicated by signals "W1", "W2", "W3", "W4", and "W5", all of the mock defects can be detected.

Figure 24:
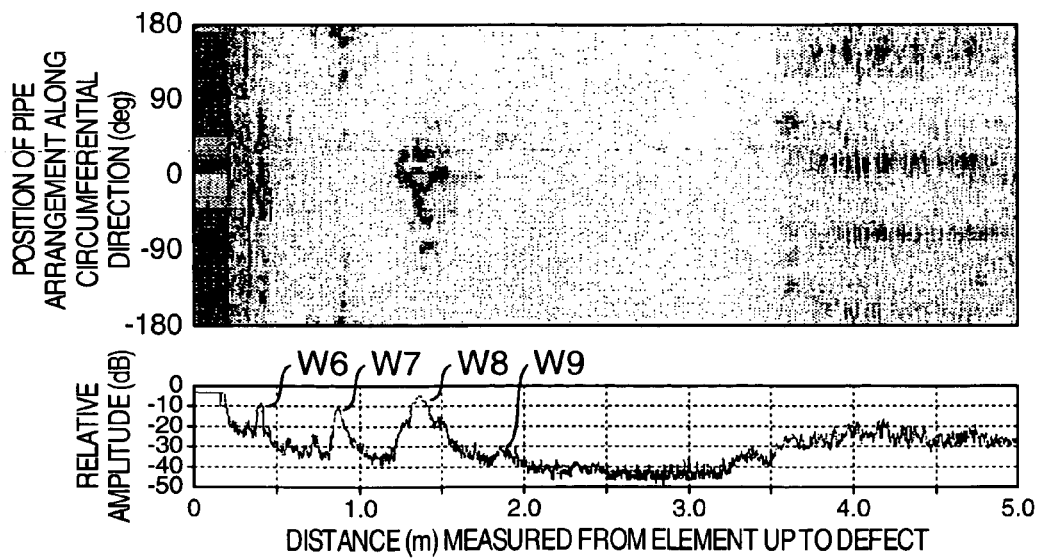
FIG. 24 is an explanatory diagram for explaining that positions of reflection waveforms are displayed on a plane where a pipe arrangement is extended when a pipe arrangement having an outer diameter of 114.3 mm and a pipe wall thickness of 6 mm, to which a defect has been applied, is inspected by such a guided wave in an L(0, 2) mode and having a center frequency of 500 KHz by employing the conventional pipe arrangement inspecting apparatus of the fourth embodiment.

FIG. 24 indicates a test result which has been measured by employing the conventional transmission method for a comparison purpose, under such a condition that such a tone burst wave having a frequency of 500 KHz for 4 cycles is employed as the transmission waveform. In this drawing, signals W6, W7, W8, and W9 correspond to reflection waveforms which are reflected from the respective defects D1, D2, D3, D4. Although the relatively large defects may be detected, the smallest defect "D5" cannot be detected.

In accordance with the above-described pipe arrangement inspecting apparatus of the fourth embodiment of the present invention, while the pipe arrangement explained in the second embodiment of the present invention is subdivided into a plurality of the inspection segments along the axial direction, the received signals are coupled to each other, which are acquired by transmitting/receiving the transmission signals. These transmission signals are different from each other every subdivided inspection segment. In addition to the above-described function, the fourth embodiment can achieve the following effect. That is, while the plural guided wave transmitting/receiving elements are arranged, these guided wave transmitting/receiving elements are switched so as to transmit/receive the guided waves, and then the respective received signals are synthesized with each other in order to form the inspection image. As a consequence, the positions of the defects along the circumferential direction can be measured, and also, such an inspection result which can be easily and visibly recognized can be acquired.

Figure 25:
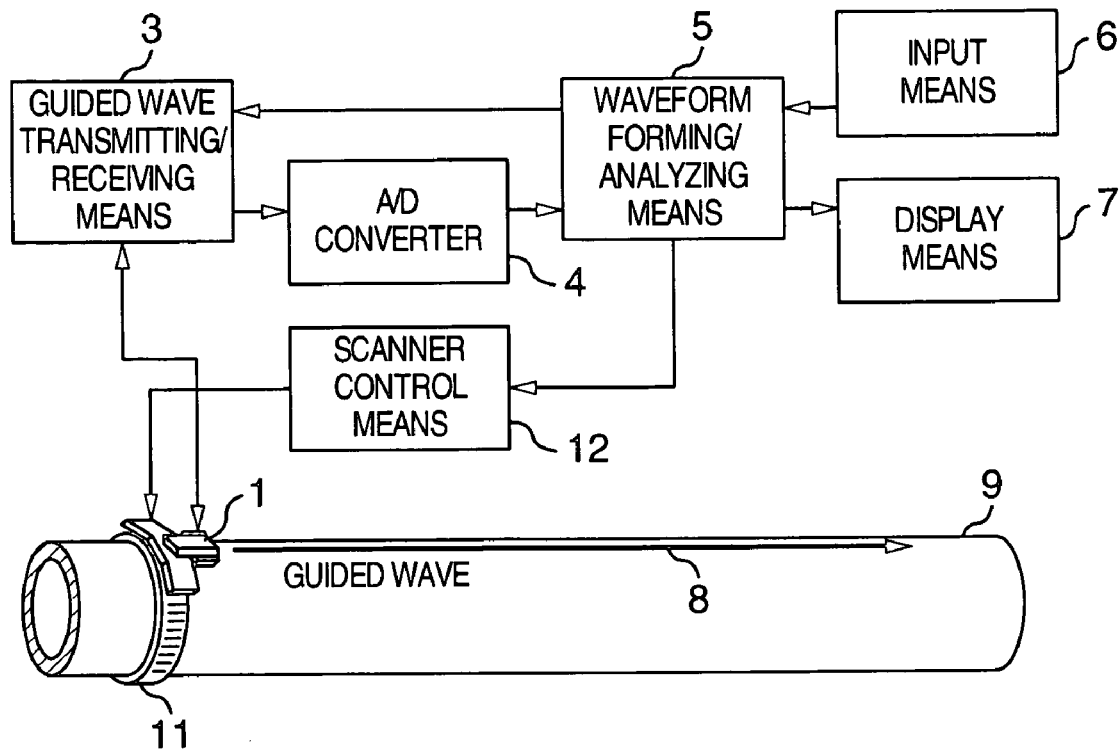
FIG. 25 is a schematic block diagram for showing an arrangement of a pipe arrangement inspecting apparatus according to a fifth embodiment of the present invention.

Next, a pipe arrangement inspecting apparatus according to a fifth embodiment of the present invention will now be explained with reference to FIG. 25. FIG. 25 is a schematic block diagram for indicating an arrangement of a pipe arrangement inspecting apparatus according to the fifth embodiment of the present invention. In this drawing, reference numeral 11 shows a scanning mechanism; reference numeral 12 indicates a scanner control means, and other constructions are the same as those of the first embodiment of the present invention. Since a sequential operation for detecting a reduced wall thickness which occurs in a pipe arrangement in accordance with this fifth embodiment is similar to that of the third embodiment of the present invention, explanations thereof are omitted. The fifth embodiment owns a technical different from that of the third embodiment as follows: That is, this pipe arrangement inspecting apparatus is equipped with the scanning mechanism 11 for gripping a single set of the guided wave transmitting/receiving element 1, so that a plurality of inspection segments arranged along the circumferential direction can be measured by that this scanning mechanism 11 scans the pipe arrangement along the circumferential direction.

In accordance with the above-described pipe arrangement inspecting apparatus of the fifth embodiment of the present invention, since the same guided wave transmitting/receiving element 1 is utilized by a plurality of circumferential segments, fluctuations contained in the inspection result can be suppressed. Furthermore, there is another effect that the cost required for the guided wave transmitting/receiving element can be suppressed. In particular, this fifth embodiment may become useful in such a case that a total number of circumferential segments is wanted to be increased.

As preciously described in detail, in accordance with the nondestructive inspection apparatus and the nondestructive inspection method of the present invention, even in such a case that the higher frequency range is utilized for the nondestructive inspection, in which the group velocities of the guided waves are not made constant, the long distance sections can be inspected in the batch manner in the higher sensitivities.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A nondestructive inspection apparatus using a guided wave, comprising:
    waveform forming means for forming a transmission waveform by employing a reference waveform;
    a transmitting element for generating a guided wave within an object under inspection based upon said transmission waveform;
    a receiving element for receiving a reflection wave of said guided wave from an inspection region of said object under inspection;
    analyzing means for outputting inspection information which is acquired based upon the reception waveform of said reflection wave received by said receiving element; and
    display means for displaying thereon said inspection information,
    wherein said waveform forming means further comprises:
    means for computing a calculated waveform from said reference waveform which propagates as said guided wave over a total distance between said transmitting element and said inspection region and between said inspection region and said receiving element; and means for forming the transmission waveform by applying time-inversion to said calculated waveform.

2. A nondestructive inspection apparatus using a guided wave, as claimed in claim 1 wherein:
    both said transmitting element and said receiving element correspond to the same element which is employed when said guided wave is generated and when said reflection wave is received.

3. A nondestructive inspection apparatus using a guided wave, as claimed in claim 1 wherein:
    said display means comprises: means for displaying thereon said transmission waveform.

4. A nondestructive inspection apparatus using a guided wave, as claimed in claim 1 wherein:
    said object under inspection corresponds to a pipe arrangement; and said nondestructive inspection apparatus further comprises: a scanner for mechanically scanning both said transmitting element and said receiving element along a circumferential direction of said pipe arrangement.

5. A nondestructive inspection apparatus using a guided wave, as claimed in claim 1 wherein:
    said object under inspection corresponds to a pipe arrangement; said analyzing means comprises: an arrangement in which information of an inspection image is formed which is displayed on a plane where said inspection result is expanded along the circumferential direction of said pipe arrangement, and a picture signal of said information is outputted; and said display means comprises: an arrangement for receiving said information so as to display said inspection image.

6. A nondestructive inspection apparatus using a guided wave, comprising:
    waveform forming means for forming a transmission waveform by employing a reference waveform;
    a transmitting element for generating a guided wave within an object under inspection based upon said transmission waveform;
    a receiving element for receiving a reflection wave of said guided wave from an inspection region of said object under inspection;
    analyzing means for outputting inspection information which is acquired based upon the reception waveform of said reflection wave received by said receiving element; and
    display means for displaying thereon said inspection information, wherein said waveform forming means comprises: means for forming at least one transmission waveform with respect to each of inspection segments, while the inspection region of said object under inspection is subdivided into a plurality of said inspection segments along a propagation direction of said guided wave.

7. A nondestructive inspection apparatus using a guided wave, as claimed in claim 6 wherein:
    said analyzing means comprises: means for extracting a reception wave portion of a time region corresponding to a certain distance of said inspection segment from said reception waveform, and for coupling said extracted reception wave portions to each other so as to form a reception waveform of an entire region of said inspection regions.

8. A nondestructive inspection method comprising:
    a step of calculating reception waveforms when an arbitrary waveform propagates as a guided wave for a predetermined distance;
    a step for forming a transmission waveform by employing a reference waveform;
    a step for generating a guided wave within an object under inspection based upon said transmission waveform;
    a step for receiving a reflection wave of said guided wave from an inspection region of said object under inspection by a receiving element;
    a step for acquiring inspection information which is acquired based upon the reception waveform of said reflection wave received by said receiving element; and
    a step for displaying thereon said inspection information, wherein said waveform forming means further comprises: means for computing a calculated waveform from said reference waveform which propagates as said guided wave over a total distance between said transmitting element and said inspection region and between said inspection region and said receiving element; and means for forming the transmission waveform by applying time-inversion to said calculated waveform.

9. A nondestructive inspection method as claimed in claim 8 wherein:
    a relationship between a frequency of said transmission waveform and a thickness of said object under inspection is capable of satisfying such a condition that:

frequency (MHz)×thickness (mm)≧0.5, and also,
    frequency (MHz)×thickness (mm)≦4.0.

10. A nondestructive inspection method comprising:
    a step for forming a transmission waveform by employing a reference waveform;
    a step for generating a guided wave within an object under inspection based upon said transmission waveform;
    a step for receiving a reflection wave of said guided wave from an inspection region of said object under inspection by a receiving element;
    a step for acquiring inspection information which is acquired based upon the reception waveform of said reflection wave received by said receiving element;
    a step for displaying thereon said inspection information;

a step for subdividing the inspection region of said object under inspection into a plurality of inspection segments along a propagation direction of said guided wave;

a step for forming said transmission waveforms every said inspection segment by setting said inspection segment as the inspection region, and for allocating at least one transmission waveform with respect to at least one of said inspection segments;

a step for receiving a reflection waveform from every said inspection segment by employing said allocated transmission wave; and a step for extracting a reception waveform portion reflected from the position corresponding to said inspection segment from said received reflection wave.

11. A nondestructive inspection method as claimed in claim 10 wherein:

a relationship between a frequency of said transmission waveform and a thickness of said object under inspection is capable of satisfying such a condition that:

frequency (MHz)×thickness (mm)≧0.5, and also,
frequency (MHz)×thickness (mm)≦4.0.

12. A nondestructive inspection method as claimed in claim 10, further comprising:

a step for coupling said extracted reception waveform portions to each other so as to acquire a coupled reception waveform.

13. A nondestructive inspection method as claimed in claim 12 wherein:

a relationship between a frequency of said transmission waveform and a thickness of said object under inspection is capable of satisfying such a condition that:

frequency (MHz)×thickness (mm)≧0.5, and also,
frequency (MHz)×thickness (mm)≦4.0.

14. A nondestructive inspection method as claimed in claim 12 wherein:

said object under inspection corresponds to a pipe arrangement; and said nondestructive inspection method further comprises:

a step for subdividing the inspection region of said pipe arrangement into a plurality of circumferential segments along a circumferential direction;

a step for acquiring said reception wave every said circumferential segment; and a step for acquiring said coupled reception waveform every said circumferential segment.

15. A nondestructive inspection method as claimed in claim 14 wherein:

a relationship between a frequency of said transmission waveform and a thickness of said object under inspection is capable of satisfying such a condition that:

frequency (MHz)×thickness (mm)≦0.5, and also,
frequency (MHz)×thickness (mm)≦4.0.

16. A nondestructive inspection method as claimed in claim 14, further comprising:

a step for displaying the inspection result with employment of said coupled reception waveform acquired every said circumferential segment on a plane expanded view of said pipe arrangement.

17. A nondestructive inspection method as claimed in claim 16 wherein:

a relationship between a frequency of said transmission waveform and a thickness of said object under inspection is capable of satisfying such a condition that:

frequency (MHz)×thickness (mm)≧0.5, and also,
frequency (MHz)×thickness (mm)≦4.0.

18. A nondestructive inspection apparatus using a guided wave, comprising:

waveform forming means for forming a transmission waveform by employing a reference waveform;

a transmitting element for generating a guided wave within an object under inspection based upon said transmission waveform;

a receiving element for receiving a reflection wave of said guided wave from an inspection region of said object under inspection;

analyzing means for outputting inspection information which is acquired based upon the reception waveform of said reflection wave received by said receiving element; and display means for displaying thereon said inspection information, wherein said waveform forming means further comprises: means for computing a calculated waveform from said reference waveform which propagates as said guided wave over a total distance between said transmitting element and said inspection region and between said inspection region and said receiving element: and means for forming the transmission waveform by applying time-inversion to said calculated waveform, and wherein said object under inspection corresponds to a pipe arrangement; a plurality of both said transmitting element and said receiving element and wherein said receiving element is arranged around said pipe arrangement in a ring shape; and said nondestructive inspection apparatus further comprises: element switching means for switching connections made between said transmitting elements and said receiving elements with respect to both said guided wave transmitting means and said guided wave receiving means.

* * * * *